US008177715B2

(12) United States Patent
Chiba et al.

(10) Patent No.: US 8,177,715 B2
(45) Date of Patent: May 15, 2012

(54) CAPSULE MEDICAL SYSTEM AND BIOLOGICAL INFORMATION ACQUIRING METHOD

(75) Inventors: Atsushi Chiba, Hachioji (JP); Akio Uchiyama, Yokohama (JP); Hironobu Takizawa, Hino (JP); Ryoji Sato, Hino (JP); Atsushi Kimura, Akiruno (JP); Tetsuo Minai, Hachioji (JP); Takeshi Mori, Machida (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 673 days.

(21) Appl. No.: 12/324,979

(22) Filed: Nov. 28, 2008

(65) Prior Publication Data
US 2009/0137883 A1  May 28, 2009

(30) Foreign Application Priority Data
Nov. 28, 2007  (JP) .................. 2007-307877

(51) Int. Cl.
*A61B 5/00* (2006.01)
(52) U.S. Cl. ........ 600/301; 600/302; 600/309; 600/372; 600/382; 600/393; 600/424; 600/593
(58) Field of Classification Search .................. 600/302, 600/301, 309, 372, 382, 393, 424, 593
See application file for complete search history.

(56) References Cited

U.S. PATENT DOCUMENTS

| 5,604,531 | A * | 2/1997 | Iddan et al. ...................... 348/76 |
| 6,473,635 | B1 | 10/2002 | Rasche |
| 7,160,258 | B2 * | 1/2007 | Imran et al. .................... 600/593 |
| 7,580,739 | B2 | 8/2009 | Minai et al. |
| 2002/0193669 | A1 * | 12/2002 | Glukhovsky .................. 600/302 |
| 2005/0143648 | A1 | 6/2005 | Minai et al. |
| 2006/0173265 | A1 | 8/2006 | Kim et al. |

FOREIGN PATENT DOCUMENTS

| CN | 1741766 A | 3/2006 |
| CN | 1878495 A | 12/2006 |
| EP | 0 667 115 A1 | 8/1995 |
| EP | 1 088 514 A1 | 4/2001 |
| JP | 2006-513001 | 4/2006 |
| WO | WO 2004/066833 | 8/2004 |
| WO | WO 2008/026549 A1 | 3/2008 |

OTHER PUBLICATIONS

Abstract only of U.S. Patent Application No. US 2006/173265 A1.

* cited by examiner

*Primary Examiner* — Chris L Chin
(74) *Attorney, Agent, or Firm* — Scully, Scott, Murphy & Presser, P.C.

(57) ABSTRACT

A capsule medical system is provided with a capsule medical device to be inserted into a subject, at least one electrode pad having a plurality of receiving electrodes, a receiving electrode switching unit, a control unit for controlling operations of the receiving electrode switching unit, and a position detector. The capsule medical device has a biological information acquiring unit for acquiring biological information of the subject, and a transmitting unit for outputting the biological information from a transmitting electrode through a living body. At least one electrode pad detects the biological information by a plurality of receiving electrodes. The receiving electrode switching unit switches a pair of receiving electrodes among the plurality of receiving electrodes. The position detector detects a position of the capsule medical device inside the subject based on the biological information detected by the electrode pad, and position coordinate data of the plurality of receiving electrodes.

14 Claims, 16 Drawing Sheets

CAPSULE ENDOSCOPE 2

CAPSULE MEDICAL SYSTEM AND BIOLOGICAL INFORMATION ACQUIRING METHOD

REFERENCE OF THE RELATED APPLICATION

This application is based upon and claims the benefit of priority from Japanese Patent Application No. 2007-307877, filed Nov. 28, 2007, the entire contents of which are incorporated herein by reference.

BACKGROUND OF THE INVENTION

1. Field of the Invention

The present invention relates to a capsule medical system and a biological information acquiring method for performing human body communications with a capsule medical device inserted into the inside of a subject, such as a patient, to thereby acquire information in the body of the subject.

2. Description of the Related Art

In the field of endoscopes, a swallowable capsule endoscope (one example of a capsule medical device) has appeared in recent years. This capsule endoscope is provided with an imaging function and a radio communication function. After the capsule endoscope is swallowed from a mouth of a subject (hereinafter, it may also be called a human body) such as a patient or the like, for observations (examinations) until it is naturally excreted to the outside of the body, the capsule endoscope sequentially captures information in the body of the subject, for example, images inside internal organs (hereinafter, they may also be called in-vivo images) while moving inside the internal organs, such as a stomach, a small intestine, and the like, by peristaltic movements.

However, since this capsule endoscope is communicating with the outside of the human body by the radio communication function, the power dissipation is increased, the operating time is decreased, and a volume occupied by a primary battery is also increased, so that there has been a problem that reduction in size and improvement in performance of the capsule endoscope are inhibited. Consequently, a human body communication system in which communications between the capsule endoscope inside the human body and a receiving apparatus outside the human body (i.e., human body communications) are performed using the human body as a communication medium has appeared in recent years (refer to Patent Application Publication No. 2006-513001).

In such a human body communication system, currents are generated according to a potential difference between transmitting electrodes formed on a surface of the capsule endoscope, and when the currents flow through the human body, a voltage is induced between two receiving electrodes provided on a surface of the human body, and the receiving apparatus outside the human body receives image signals from the capsule endoscope by this induced voltage. The capsule endoscope that performs the human body communications can transmit image data at a low frequency signal of about 10 MHz without requiring an RF signal of several hundreds of MHz, so that the power dissipation can be reduced extremely.

Moreover, if a position detecting technology for detecting a position of the capsule endoscope inside the human body based on the voltage induced between the receiving electrodes, and the human body communication system are combined by the human body communications, it is possible to achieve a capsule medical system that can acquire in-vivo images of the subject from the capsule endoscope by the human body communications and also detect a position of the capsule endoscope inside the human body upon capturing the in-vivo images.

SUMMARY OF THE INVENTION

A capsule medical system according to an aspect of the present invention includes a capsule medical device comprising a biological information acquiring unit for acquiring biological information of a subject, and a transmitting unit for outputting the biological information from a transmitting electrode through a living body; at least one electrode pad comprising a plurality of receiving electrodes for detecting the biological information; a receiving electrode switching unit that switches a pair of receiving electrodes among the plurality of receiving electrodes; a control unit that controls operations of the receiving electrode switching unit; and a position detector that detects a position of the capsule medical device within the subject based on the biological information detected by the electrode pad and position coordinate data of the plurality of receiving electrodes.

A biological information acquiring method according to another aspect of the present invention includes selecting a pair of receiving electrodes for each of electrode pads for detecting biological information within a subject; and calculating at least one of a position and a direction of a capsule medical device within the subject based on a voltage between the selected pair of receiving electrodes and position coordinate data of an electrode group of electrode pads including the pair of receiving electrodes.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule medical system and a biological information acquiring method according to the present invention will be described below. It is to be noted that although a capsule endoscope that captures in-vivo images which is one example of subject information and also transmits the in-vivo images through human body communications will be hereinafter illustrated as one example of a capsule medical device used for the capsule medical system in accordance with the present invention, the present invention is not limited by the embodiments.

Figure 1:
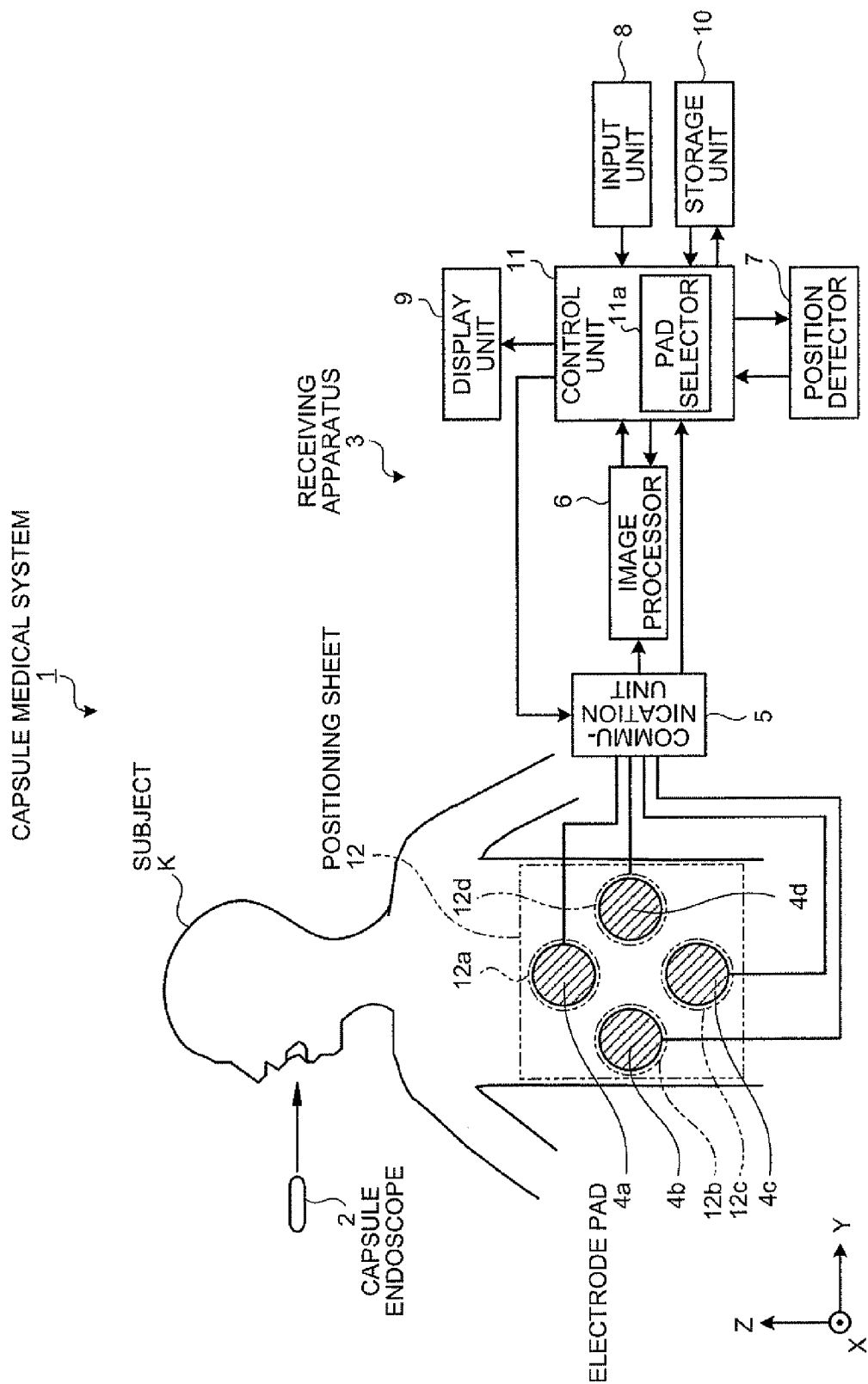
FIG. 1 is a block diagram schematically showing one configuration example of a capsule medical system in accordance with a first embodiment of the present invention.

FIG. 1 is a block diagram schematically showing one configuration example of a capsule medical system in accordance with a first embodiment of the present invention. As shown in FIG. 1, a capsule medical system 1 in accordance with the first embodiment is provided with a capsule endoscope 2 for acquiring subject information of a subject K such as a patient or the like, and a receiving apparatus 3 for receiving the subject information that the capsule endoscope 2 inserted into the body of the subject K transmits by performing human body communications. The receiving apparatus 3 is provided with a plurality of electrode pads 4a to 4d for detecting the subject information that is transmitted by the capsule endoscope 2 through the human body communications, a communication unit 5 for performing the human body communications with the capsule endoscope 2 inside the subject K via the electrode pads 4a to 4d, an image processor 6 for acquiring the in-vivo images of the subject K which is the subject information based on the data received by the communication unit 5, and a position detector 7 for detecting at least one of a position and a direction of the capsule endoscope 2 inside the body of the subject K. The receiving apparatus 3 is also provided with an input unit 8 for receiving a variety of information, a display unit 9 for displaying a variety of information, such as the in-vivo images of the subject K or the like, a storage unit 10 for storing a variety of information, such as the in-vivo images of the subject K or the like, and a control unit 11 for controlling each component part of the receiving apparatus 3.

The capsule endoscope 2 is one example of the capsule medical device to be inserted into internal organs of the subject K for acquiring the subject information of the subject K, and it has an imaging function for capturing the in-vivo images which are one example of the subject information, and a human body communicating function for performing communications with the receiving apparatus 3 outside the human body using the human body (subject K) as a communication medium. Specifically, when being inserted into the body of the subject K, the capsule endoscope 2 captures the in-vivo images of the subject K while moving the inside of the internal organs of the subject K by peristaltic movements or the like, and performs the human body communications for transmitting the captured in-vivo images to the receiving apparatus 3 outside the subject K. The in-vivo images that are transmitted by the human body communications of the capsule endoscope 2 are received by the receiving apparatus 3 via any one of a plurality of electrode pads 4a to 4d. Whenever the capsule endoscope 2 captures the in-vivo images of the subject K, it repeatedly performs the human body communications with the receiving apparatus 3 and sequentially transmits the in-vivo images of the subject K to the receiving apparatus 3.

The electrode pads 4a to 4d respectively have electrode groups for detecting the subject information transmitted by the capsule endoscope 2 through the human body communications, and are fixedly arranged onto a body surface of the subject K in a form of contacting the electrode groups to the body surface of the subject K. In addition, each of the electrode pads 4a to 4d has an A/D conversion processing function for converting the subject information detected by the electrode groups into digital data, and sends out the obtained digital data to the communication unit 5 via a cable. The internal configurations of the electrode pads 4a to 4d will be hereinafter described.

The electrode pads 4a to 4d are fixedly arranged onto the body surface of the subject K using a positioning seat 12 suitable for the physical constitution of the subject K. Specifically, the positioning seat 12 has openings 12a to 12d formed to be matched with an outside shape (for example, circle as shown in FIG. 1) of the electrode pads 4a to 4d, and is arranged on the body surface of the subject K. As for the positioning seat 12, local parts which are within the body surface of the subject K, and whose position coordinates in a Cartesian coordinate system XYZ are known are specified by the openings 12a to 12d, respectively. The Cartesian coordinate system XYZ is a three-axis Cartesian coordinate system fixed to a supporting member (not shown) of the subject K, the bed for supporting the subject K, or the like, for example. The electrode pads 4a to 4d are fixedly arranged at respective positions specified by the openings 12a to 12d of the positioning seat 12. In this case, respective directions of the electrode pads 4a to 4d are fixed to the subject K by respectively aligning predetermined positions of the electrode pads 4a to 4d with marks (not shown) that are given at respective vicinities of the openings 12a to 12d of the positioning seat 12, for example. As a result of that, the electrode pads 4a to 4d fixedly arrange the electrode groups for human body communications at a plurality of local parts, which are within the body surface of the subject K, and whose position coordinates are known, respectively. It is to be noted that the positioning seat 12 may be removed from the subject K after thus fixedly arranging the electrode pads 4a to 4d on the body surface of the subject K.

The communication unit 5 performs the human body communications with the capsule endoscope 2 inside the subject K via the electrode pads 4a to 4d that are fixedly arranged onto the body surface of the subject K. Specifically, the communication unit 5 is connected with the electrode pads 4a to 4d via the cables (not shown), receives the digital data outputted by the electrode pads 4a to 4d via the cables, and sends out the received digital data to the image processor 6 and the control unit 11. In this case, the communication unit 5 sequentially receives from the electrode pads 4a to 4d the digital data of a voltage detected by each electrode group of the electrode pads 4a to 4d, and sequentially sends out the digital data of the obtained voltage to the control unit 11.

Additionally, the communication unit 5 performs demodulation processing or the like to digital data with the highest voltage among the digital data to thereby demodulate the digital data of the in-vivo images of the subject K. The communication unit 5 sends out the digital data of the in-vivo images to the image processor 6. Moreover, the communication unit 5 acquires control signals from the control unit 11, and sequentially transmits the acquired control signals to the electrode pads 4a to 4d. Note that, the control signal from the control unit 11 is a control signal to cause any one of the electrode pads 4a to 4d to detect a transmission signal transmitted by the capsule endoscope 2 through the human body communications, and is sequentially transmitted to the electrode pads 4a to 4d in the given order.

The image processor 6 acquires the in-vivo images of the subject K (one example of the subject information) based on the digital data obtained by digital conversion with any one of the electrode pads 4a to 4d. Specifically, the image processor 6 acquires the digital data of the in-vivo images of the subject K from the communication unit 5, and performs predetermined image processing to the acquired digital data to thereby generate the in-vivo images of the subject K (specifically, in-vivo images captured by the capsule endoscope 2 inside the subject K). The image processor 6 sends out the generated in-vivo images to the control unit 11.

The position detector 7 detects at least one of the position and direction of the capsule endoscope 2 inside the body of the subject K based on the digital data of the voltage received by the communication unit 5 from the electrode pads 4a to 4d, and the position coordinate data of the electrode group. In this case, the position detector 7 calculates at least one of the position and direction of the capsule endoscope 2 inside the subject K (i.e., the position and direction in the Cartesian coordinate system XYZ), based on the digital data of the voltage detected by the electrode group of the electrode pad selected from the electrode pads 4a to 4d by a pad selector 11a (which will be described hereinafter) of the control unit 11, and the position coordinate data of each electrode in the electrode group. The position coordinate data of each electrode group of the electrode pads 4a to 4d is previously inputted by the input unit 8.

The input unit 8 is achieved using an input device, such as a keyboard, a mouse, or the like, and receives a variety of information and outputs it to the control unit 11 according to input operations by a user, such as a doctor, a nurse, or the like. The variety of information input through the input unit 8 into the control unit 11 includes, for example, instruction information instructed to the control unit 11, position coordinate data of each electrode group of the electrode pads 4a to 4d arranged at the fixed position and the direction to the subject K, patient information and examination information of the subject K, and the like.

Note that the patient information of the subject K is specific information for specifying the subject K, and includes patient name, patient ID, date of birth, sex, age, and the like of the subject K, for example. Meanwhile, the examination information of the subject K is specific information for specifying a capsule endoscope examination (examination for inserting the capsule endoscope 2 into the inside of the internal organ to observe the inside of the internal organ) carried out to the subject K, and includes examination ID, examination date, and the like, for example.

The display unit 9 is achieved using various displays, such as a CRT display, a liquid crystal display, or the like, and displays a variety of information instructed to display by the control unit 11. Specifically, the display unit 9 displays the in-vivo image group of the subject K captured by the capsule endoscope 2, the patient information of the subject K, the examination information of the subject K, the information for indicating the position and direction of the capsule endoscope 2 inside the subject K, and the like.

The storage unit 10 is achieved using various rewritable storage media that store data, such as RAM, EEPROM, flash memory, hard disk, or the like. The storage unit 10 stores various data in response to a write instruction by the control unit 11, and sends the data, among the stored various data, to the control unit 11 in response to a read instruction by the control unit 11. Specifically, the storage unit 10 stores the in-vivo image group of the subject K, the patient information and examination information of the subject K, the position coordinate data of each electrode group of the electrode pads 4a to 4d, and the information of the position and direction of the capsule endoscope 2 detected by the position detector 7.

The storage unit 10 is removably equipped with a portable recording medium, such as flexible disk (FD), compact disc (CD), DVD (Digital Versatile Disk), or the like, and may be achieved using a drive or the like, which performs read processing or write processing of various data to the equipped portable recording medium.

The control unit 11 controls each component part (the electrode pads 4a to 4d, the communication unit 5, the image processor 6, the position detector 7, the input unit 8, the display unit 9, and the storage unit 10) of the receiving apparatus 3, and controls input and output of signals between respective component parts. Specifically, the control unit 11 causes the capsule endoscope 2 inside the subject K and the communication unit 5 to perform the human body communications therebetween based on the instruction information input by the input unit 8, causes the display unit 9 to display desired information, such as the in-vivo images of the subject K, the position information of the capsule endoscope 2, and the like thereon, and causes the storage unit 10 to store a variety of information, such as the input information by the input unit 8, the in-vivo image group of the subject K, the position information of the capsule endoscope 2, and the like therein. Additionally, the control unit 11 sequentially transmits the control signals to the electrode pads 4a to 4d via the communication unit 5, and controls the electrode pads 4a to 4d by the control signals. In this case, the control unit 11 causes any one of the electrode pads 4a to 4d to detect the image signals transmitted by the capsule endoscope 2 through the human body communications. Specifically, the control unit 11 causes a pair of electrodes in each electrode group of the electrode pads 4a to 4d to detect a voltage induced by an electric field or a displacement current produced in the body of the subject K by the capsule endoscope 2 through the human body communications.

Moreover, the control unit 11 has the pad selector 11a that selects a suitable electrode pad for detection processing of the position and direction of the capsule endoscope 2 from a plurality of electrode pads 4a to 4d. The pad selector 11a sequentially acquires the digital data of the voltages from the electrode pads 4a to 4d via the communication unit 5. The pad selector 11a selects an electrode pad suitable for the detection processing of the position and direction of the capsule endoscope 2, i.e., an electrode pad in a position closest to the capsule endoscope 2 inside the subject K among the electrode pads 4a to 4d, based on the acquired voltage of each piece of digital data from the electrode pads 4a to 4d. The control unit 11 sends to the position detector 7 the digital data of the voltage detected by the electrode group of the electrode pad selected by the pad selector 11a, and the position coordinate data of each electrode included in the electrode group of this selected electrode pad. The control unit 11 controls the position detector 7 so as to detect the position and direction of the capsule endoscope 2 inside the subject K based on the digital data of the voltage and the position coordinate data of each electrode that have been sent out.

Figure 2:
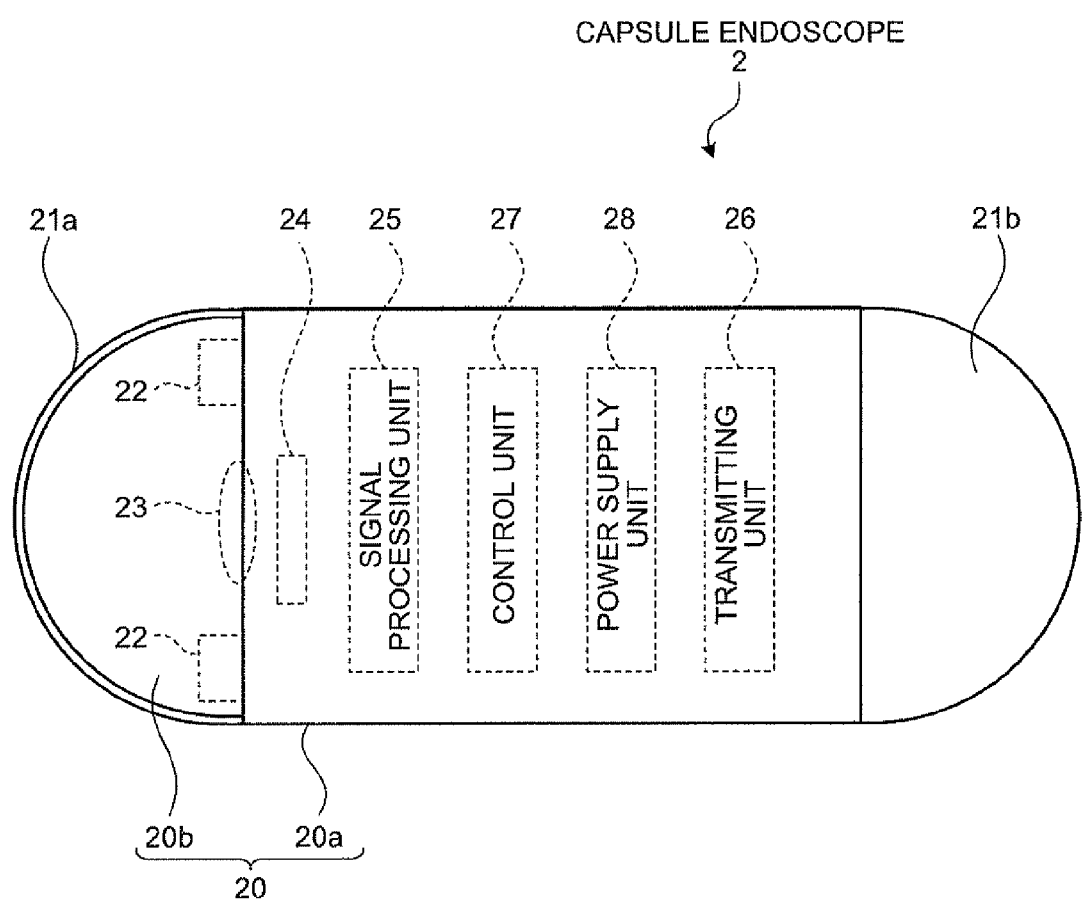
FIG. 2 is a schematic view showing one configuration example of a capsule endoscope in accordance with the first embodiment of the present invention.

Next, a configuration of the capsule endoscope 2 having the aforementioned imaging function and the human body communicating function will be described. FIG. 2 is a schematic view showing one configuration example of the capsule endoscope 2 of the capsule medical system in accordance with the first embodiment of the present invention. As shown in FIG. 2, the capsule endoscope 2 in accordance with the first embodiment is provided with a capsule-shaped casing 20 formed in a size to be easily inserted into the body of the subject K, and transmitting electrodes 21a and 21b for human body communications. Additionally, the capsule endoscope 2 is provided with illuminating units 22, such as LEDs or the like for illuminating the inside of the internal organ of the subject K, a condensing lens 23 for condensing reflected light from the inside of the internal organ illuminated by the illuminating units 22, and an imaging device 24 for receiving the reflected light condensed by the condensing lens 23 to thereby capture the in-vivo images of the subject K, inside the capsule-shaped casing 20. Further, the capsule endoscope 2 is provided with a signal processing unit 25 for processing signals outputted from the imaging device 24 to thereby generate image signals of the subject K, a transmitting unit 26 for modulating (for example, phase modulation) the image signals of the subject K, and transmitting the modulated image signals from the transmitting electrodes 21a and 21b into the human body, a control unit 27 for controlling each component part of the capsule endoscope 2, and a power supply unit 28, such as a battery or the like, for supplying electric power, inside the capsule-shaped casing 20.

The capsule-shaped casing 20 is formed by an opaque cylindrical casing 20a which has one end being an opening end and another end having a dome shape; and a transparent dome-shaped casing 20b which closes the opening end. The capsule-shaped casing 20 liquid-tightly houses internal configuration units (the illuminating unit 22, the condensing lens 23, the imaging device 24, the signal processing unit 25, the transmitting unit 26, the control unit 27, and the power supply unit 28) of the capsule endoscope 2.

Moreover, the transmitting electrodes 21a and 21b for human body communications are formed on both ends of the capsule-shaped casing 20, i.e., on an outer surface of the dome-shaped casing 20b and an outer surface of a dome-shaped portion of the cylindrical casing 20a, respectively. Specifically, the transmitting electrode 21a formed on the outer surface of the dome-shaped casing 20b is a transparent electrode achieved by ITO or the like. In addition, each of the transmitting electrodes 21a and 21b is excellent in corrosion resistance, and is a metal harmless to the human body, and the transmitting electrode 21b is achieved by SUS316L, gold, or the like, for example. The transmitting electrodes 21a and 21b will electrically be connected with the inside of the human body by the body fluid or the like.

When the capsule endoscope 2 performs the human body communications to thereby transmit the in-vivo images of the subject K, the transmitting unit 26 outputs the image signal whose polarities are reversed, to the transmitting electrodes 21a and 21b. As a result of this, a potential difference is caused between the transmitting electrodes 21a and 21b, and an electric field or a displacement current is generated in the body of the subject K. The electric field or the displacement current propagates to the body surface of the subject K via the human body, and thereby a voltage is induced between at least a pair of electrodes in each electrode group of the electrode pads 4a to 4d on the aforementioned body surface. As a result, the image signal output by the transmitting unit 26 via the transmitting electrodes 21a and 21b is detected by at least one of electrode groups of the electrode pads 4a to 4d, and is received by the receiving apparatus 3 via the electrode pads 4a to 4d.

Figure 3:
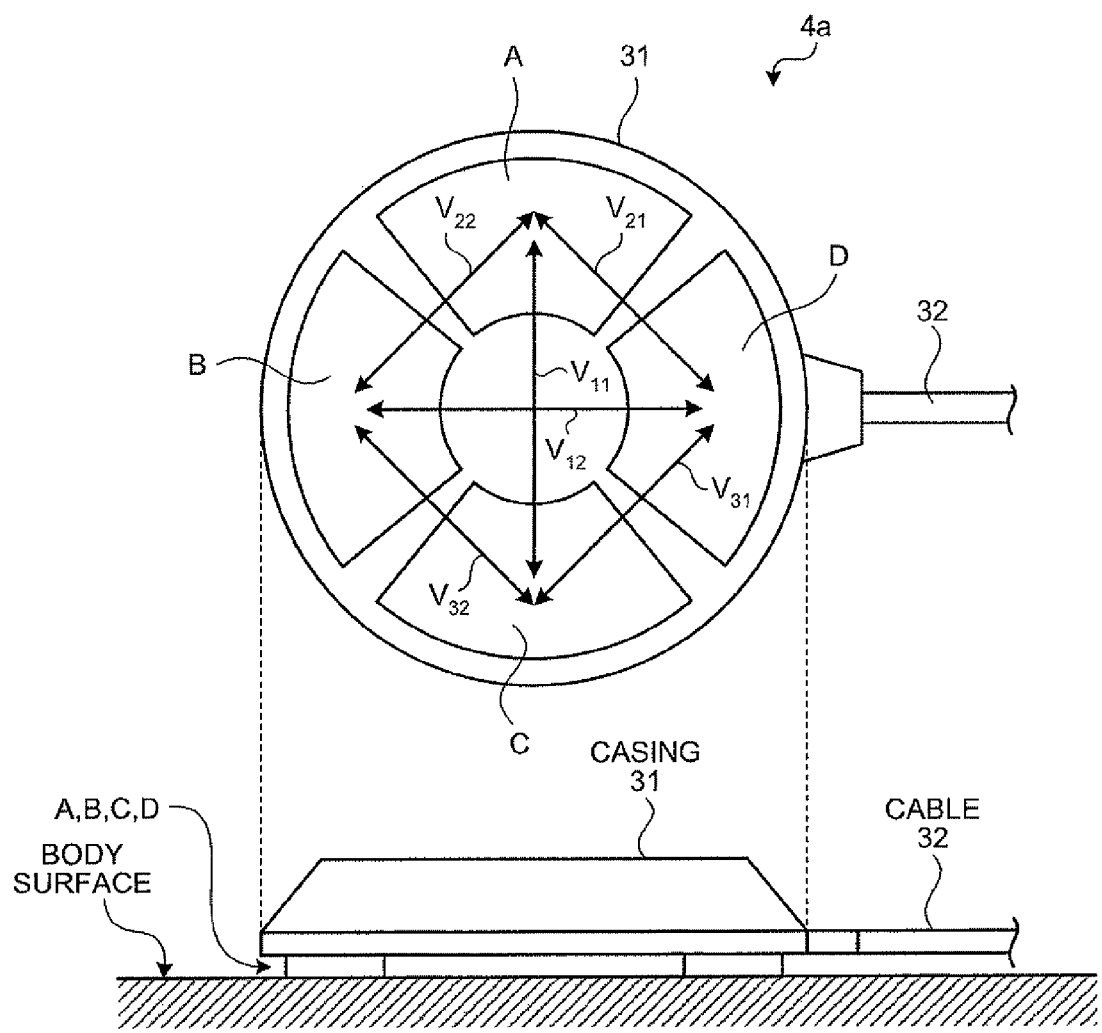
FIG. 3 is a schematic view illustrating an external configuration of an electrode pad in accordance with the first embodiment.
Figure 4:
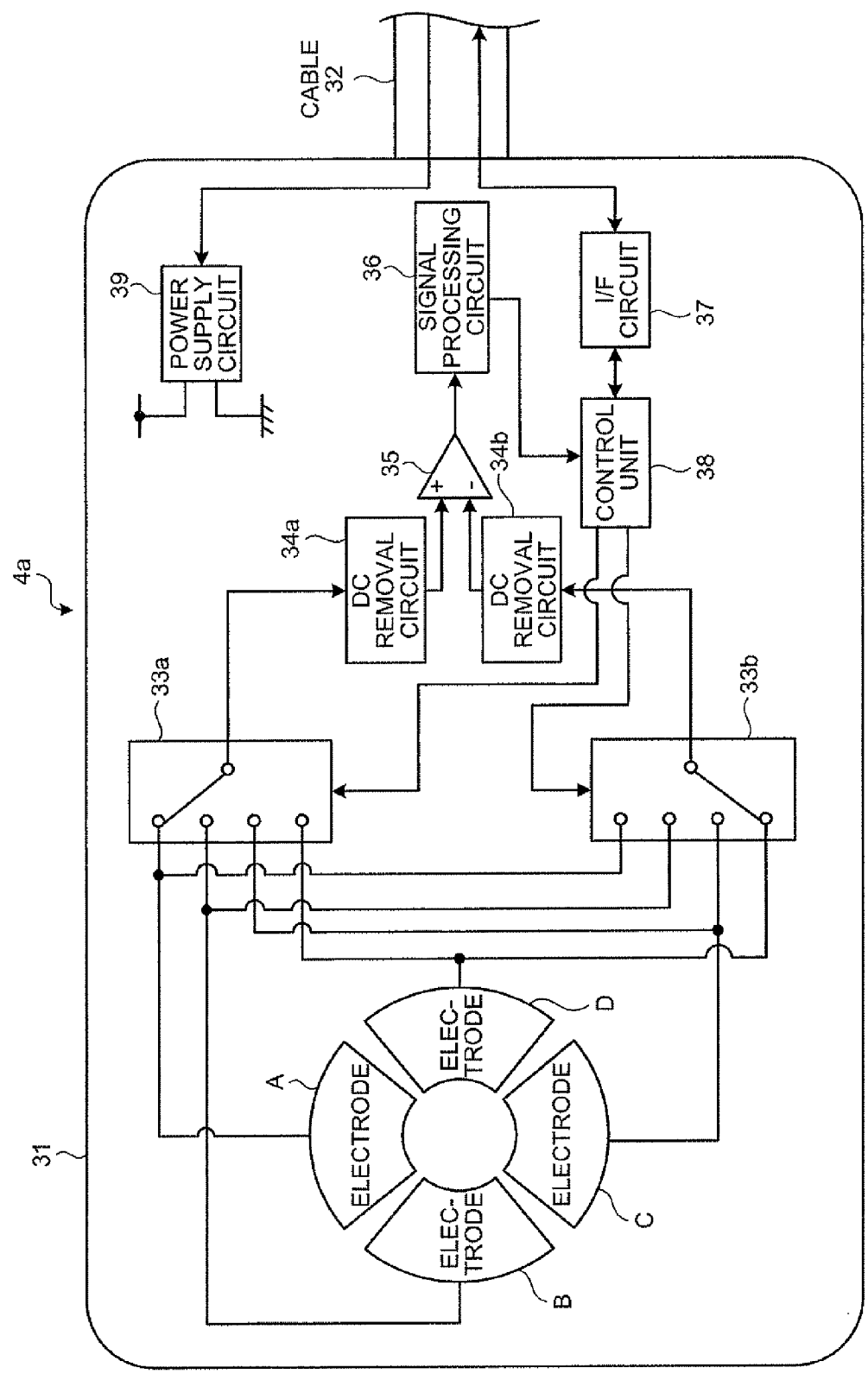
FIG. 4 is a block diagram schematically showing an internal configuration of the electrode pad in accordance with the first embodiment.

Next, a configuration of the electrode pads 4a to 4d of the capsule medical system in accordance with the first embodiment of the present invention will be described. FIG. 3 is a schematic view illustrating an external configuration of the electrode pad in accordance with the first embodiment. FIG. 4 is a block diagram schematically showing an internal configuration of the electrode pad in accordance with the first embodiment. Note that a surface (a side where the electrode group is exposed) of the electrode pad 4a, and a side surface of the electrode pad 4a in a state of being fixedly arranged onto the body surface of the subject K are shown in FIG. 3. Although a configuration of the electrode pad 4a will be hereinafter described on behalf of the plurality of electrode pads 4a to 4d, the remaining electrode pads 4b to 4d have a configuration similar to that of the electrode pad 4a. As shown in FIGS. 3 and 4, the electrode pad 4a has a plurality of electrodes A to D, which are the electrode group for the aforementioned human body communications, and is electrically connected with the communication unit 5 by a cable 32. In addition, the electrode pad 4a is provided with switching circuits 33a and 33b for selecting a pair of electrodes from a plurality of electrodes A to D, DC removal circuits 34a and 34b for removing a DC component in a signal detected by the pair of electrodes, a differential amplifier 35 for amplifying a signal whose DC component is removed by the DC removal circuits 34a and 34b, a signal processing circuit 36 for performing digital conversion of a signal (analog signal) amplified by the differential amplifier 35, an I/F circuit 37 for performing transmission and reception of signals with the communication unit 5 via the cable 32, a control unit 38 for controlling each component part of the electrode pad 4a, and a power supply circuit 39 for supplying electric power obtained via the cable 32 to each component part of the electrode pad 4a, inside a disk-shaped case 31.

The electrodes A to D are receiving electrodes for performing the human body communications with the capsule endoscope 2 inside the human body, and are arranged at the fixed position and direction to the subject K by fixedly arranging the electrode pad 4a on the body surface of the subject K as described above. In this case, the electrodes A to D are fixedly arranged at local parts, respectively, in the body surface of the subject K, and the positions and directions of the electrodes A to D are specified as known position coordinates and vector directions in the Cartesian coordinate system XYZ. Additionally, the electrodes A to D are fixedly arranged to the casing 31 in a mode of being exposed from the casing 31 of the electrode pad 4a, and contact to the body surface of the subject K when the electrode pad 4a is pasted onto the body surface of the subject K (refer to FIG. 3). A pair of electrodes among the electrodes A to D detects the image signals transmitted by the capsule endoscope 2 inside the subject K through the human body communications. In this case, a pair of electrodes among the electrodes A to D detects the potential difference (voltage) induced by the electric field or the displacement current produced by the capsule endoscope 2 as the image signals. The image signals detected by a pair of electrodes among the electrodes A to D, i.e., analog data of the voltage are respectively input into the DC removal circuits 34a and 34b via the switching circuits 33a and 33b.

Although a plurality of electrodes A to D of the electrode pad 4a may be fixedly arranged at the desired position on the outer surface of the casing 31 if the electrode pad 4a is in a mode of being able to contact with the body surface of the subject K when it is pasted onto the body surface of the subject K, it is preferable to be arranged at each position (for example, position on the same circumference) that is symmetrical with respect to a point about the center of the outer surface of this casing 31, and it is further preferable to be arranged so that directions perpendicular to each other may be included in each direction of the voltage that a pair of electrodes sequentially switched by the switching circuits 33a and 33b sequentially detects.

The switching circuits 33a and 33b are achieved using switching elements, such as a field effect transistor (FET) or the like, and selectively sequentially switch among four electrodes A to D described above a pair of electrodes that detects the transmission signal from the capsule endoscope 2 through the human body communications based on the control of the control unit 38. In this case, the switching circuit 33a and the switching circuit 33b do not mutually select the same electrode. For example, when the switching circuit 33a selects the electrode A from the electrodes A to D, the switching circuit 33b selects any one of the remaining electrodes B to D. The switching circuits 33a and 33b electrically sequentially select among four electrodes A to D a pair of electrodes that detects the image signals transmitted by the capsule endoscope 2 through the human body communications, and the switching circuit 33a sends out the analog data from one electrode of the selected pair of electrodes to the DC removal circuit 34a, while the switching circuit 33b sends out the analog data from the other electrode to the DC removal circuit 34b.

The DC removal circuits 34a and 34b remove the DC component in the signal (image signal from the capsule endoscope 2) detected by a pair of electrodes that the switching circuits 33a and 33b selected from a plurality of electrodes A to D. Specifically, the DC removal circuit 34a is electrically connected with the electrode that the switching circuit 33a selected from the electrodes A to D, and acquires the analog data of the voltage detected by the selected electrode via the switching circuit 33a. The DC removal circuit 34a removes the DC component from the acquired analog data, and subsequently sends out the analog data to the differential amplifier 35. Meanwhile, the DC removal circuit 34b is electrically connected with the electrode that the switching circuit 33b selected from the electrodes A to D, and acquires the analog data of the voltage detected by the selected electrode via the switching circuit 33b. The DC removal circuit 34b removes the DC component from the acquired analog data, and subsequently sends out the analog data to the differential amplifier 35. The differential amplifier 35 amplifies the analog data from which the DC component was removed by the DC removal circuits 34a and 34b, and sends out the amplified analog data to the signal processing circuit 36.

The signal processing circuit 36 has a function as an A/D conversion processing unit for converting into the digital data the analog data of the voltage detected by a pair of electrodes that the switching circuits 33a and 33b selected from the electrodes A to D, in other words, the subject information that the capsule endoscope 2 inside the subject K transmitted through the human body communications (in-vivo images). Specifically, the signal processing circuit 36 acquires the analog data amplified by the differential amplifier 35, performs filtering processing and A/D conversion processing to the acquired analog data, and generates digital data of the in-vivo images, which is one information example of the subject K. The digital data digital-converted by the signal processing circuit 36 is obtained by digital-converting the image signal that the capsule endoscope 2 inside the subject K transmitted through the human body communications, and is obtained by digital-converting the analog data of the voltage detected by a pair of electrodes among the electrodes A to D. The signal processing circuit 36 sends out the digital data thus generated to the control unit 38.

The I/F circuit 37 is a communication interface for performing transmission and reception of the data with the communication unit 5 via the cable 32 for connecting the communication unit 5 and electrode pad 4a. The I/F circuit 37 receives signals that the communication unit 5 transmitted via the cable 32, and transmits the received signals to the control unit 38. The signals transmitted to the I/F circuit 37 by the communication unit 5 include the control signal output by the control unit 11 of the receiving apparatus 3 in order to control the electrode pads 4a to 4d, and the like. In addition, the I/F circuit 37 transmits the digital data instructed to be transmitted by the control unit 38, to the communication unit 5 via the cable 32. It is to be noted that the digital data that the I/F circuit 37 transmits to the communication unit 5 is the digital data digital-converted by the signal processing circuit 36, in other words, the digital data of the in-vivo images of the subject K (specifically, digital data of the voltage detected by a pair of electrodes among the electrodes A to D).

The control unit 38 controls each component part of the electrode pad 4a. Specifically, the control unit 38 controls each switching operation of the switching circuits 33a and 33b for selecting a pair of electrodes from the electrodes A to D, and digital data transmitting operation of the I/F circuit 37 via the cable 32, and also controls input and output of signals between each component parts of the electrode pad 4a. When the control signal from the control unit 11 of the receiving apparatus 3 is received via the I/F circuit 37, the control unit 38 selects a pair of electrodes from the electrodes A to D based on this control signal, and also controls the switching circuits 33a and 33b so as to sequentially switch a pair of electrodes at a predetermined interval. In this case, the control unit 38 controls the switching operations of the switching circuits 33a and 33b so that the switching circuit 33a and the switching circuit 33b do not simultaneously select the same electrode. Meanwhile, the control unit 38 controls the I/F circuit 37 based on the control signal from the control unit 11 received via the I/F circuit 37 so as to transmit the digital data digital-converted by the signal processing circuit 36 to the communication unit 5 via the cable 32.

It is to be noted that when not receiving the control signal from the control unit 11 of the receiving apparatus 3, the control unit 38 may control the switching circuits 33a and 33b to be in an off-state (state where neither of the electrodes A to D is selected) to cause a pair of electrodes among the electrodes A to D not to detect the image signals from the capsule endoscope 2. In other words, only when receiving an instruction of signal detection by the control signal from the control unit 11 of the receiving apparatus 3, the control unit 38 may control the switching circuits 33a and 33b so that a pair of electrodes among the electrodes A to D may detect the image signals from the capsule endoscope 2.

Figure 5:
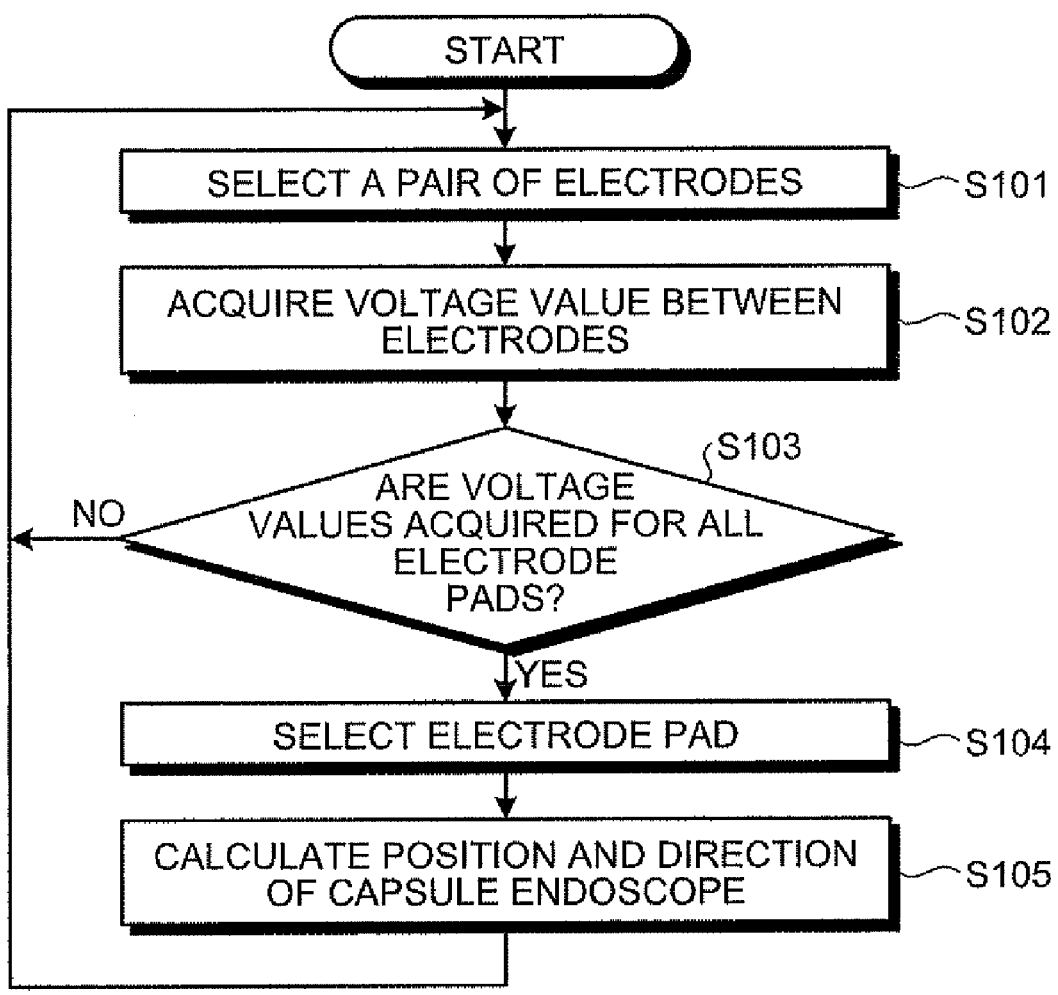
FIG. 5 is a flow chart illustrating a procedure of a control unit that causes a position detector to detect a position and a direction of the capsule endoscope inside a human body.

Next, a procedure of the control unit 11 that causes the position detector 7 to detect the position and direction of the capsule endoscope 2 inside the body of the subject K, in the receiving apparatus 3 outside the subject K will be described. FIG. 5 is a flow chart illustrating the procedure of the control unit 11 that causes the position detector 7 to detect the position and direction of the capsule endoscope 2 inside the human body. The control unit 11 of the receiving apparatus 3 causes the position detector 7 to detect the position and direction of the capsule endoscope 2 inside the body of the subject K, based on the digital data of the voltage that the electrode group included in any one of the electrode pads 4a to 4d fixedly arranged onto the body surface of the subject K detected and the position coordinate data of the electrode group.

Specifically, as shown in FIG. 5, the control unit 11 controls the electrode pads 4a to 4d so as to select a pair of electrodes that detects the induced voltage through the human body communications of the capsule endoscope 2 inside the subject K for every electrode pad (Step S101). In this case, the control unit 11 sequentially transmits the control signals to the electrode pads 4a to 4d via the communication unit 5, and causes the electrode pads 4a to 4d to switch a pair of electrodes among the electrodes A to D, respectively.

Next, the control unit 11 acquires a voltage between a pair of electrodes in each electrode group of the electrode pads 4a to 4d (Step S102). Specifically, the control unit 11 sequentially acquires from the electrode pads 4a to 4d via the communication unit 5 each piece of digital data of the voltage detected by a pair of electrodes that are selected for every electrode pad at Step S101.

Subsequently, the control unit 11 determines whether or not all the electrode pads 4a to 4d fixedly arranged onto the body surface of the subject K have completed to acquire the voltages (Step S103). If a pair of electrodes which should detect the induced voltage through the human body communications of the capsule endoscope 2 remains in each electrode group of the electrode pads 4a to 4d, the control unit 11 determines that acquisition of the voltage has not completed (Step S103, No). In this case, the control unit 11 returns to Step S101, and repeats the procedure after this Step S101.

Meanwhile, if all the voltages between a pair of electrodes required for detection of the position and direction of the capsule endoscope 2 inside the body of the subject K are acquired, the control unit 11 determines that acquisition of the voltage is completed (Step S103, Yes). Subsequently, the control unit 11 selects among all the electrode pads 4a to 4d an electrode pad that has detected the voltage required for the detection of the position and direction of the capsule endoscope 2 (Step S104). At Step S104, the pad selector 11a selects an electrode pad corresponding to the highest voltage, in other words, an electrode pad in a position closest to the capsule endoscope 2 inside the subject K, based on all the digital data of the voltages acquired from the electrode pads 4a to 4d.

Next, the control unit 11 causes the position detector 7 to calculate the position and direction of the capsule endoscope 2 inside the body of the subject K (Step S105). At Step S105, the control unit 11 sends out to the position detector 7 the digital data of each voltage detected for every pair of electrodes by the electrode group of the electrode pad that the pad selector 11a selected from the electrode pads 4a to 4d, and the position coordinate data of the electrode group of the electrode pad, and also causes the position detector 7 to calculate the position and direction of the capsule endoscope 2 inside the body of the subject K based on the digital data of each voltage and position coordinate data of the electrode group.

The position detector 7 detects the position and direction of the capsule endoscope 2 based on the control of the control unit 11, and sends out the detected position information and direction information to the control unit 11. The control unit 11 acquires the position information and direction information of the capsule endoscope 2 detected by the position detector 7, and causes the storage unit 10 to store the acquired position information and direction information. Subsequently, the control unit 11 returns to Step S101, and repeats the procedure after Step S101.

Selection process of the electrode pad performed by the pad selector 11a at Step S104 will specifically be described. The control unit 11 controls the communication unit 5 to acquire the digital data of all the voltages detected by each electrode group of the electrode pads 4a to 4d from the electrode pads 4a to 4d. Based on the digital data of all the voltages acquired from the electrode pads 4a to 4d, the pad selector 11a selects among the electrode pads 4a to 4d an electrode pad that detected the voltage required for the detection of the position and direction of the capsule endoscope 2, in other words, an electrode pad in a position closest to the capsule endoscope 2 inside the subject K.

Specifically, the control unit 11 acquires each piece of digital data of voltages $V_{11}$, $V_{12}$, $V_{21}$, $V_{22}$, $V_{31}$, and $V_{32}$ from each of the electrode pads 4a to 4d via the communication unit 5. The voltage $V_{11}$ is a voltage detected by a pair of electrodes A and C; the voltage $V_{12}$ is a voltage detected by a pair of electrodes B and D; the voltage $V_{21}$ is a voltage detected by a pair of electrodes A and D; the voltage $V_{22}$ is a voltage detected by a pair of electrodes A and B; the voltage $V_{31}$ is a voltage detected by a pair of electrodes C and D; and the voltage $V_{32}$ is a voltage detected by a pair of electrodes C and B (refer to FIG. 3). In addition, a direction of detection voltage by a pair of electrodes A and C and a voltage direction of detection voltage by a pair of electrodes B and D are perpendicular to each other; a direction of detection voltage by a pair of electrodes A and D and a voltage direction of detection voltage by a pair of electrodes A and B are perpendicular to each other; and a direction of detection voltage by a pair of electrodes C and D and a voltage direction of detection voltage by a pair of electrodes C and B are perpendicular to each other. It is to be noted that all of the pair of electrodes A and C, the pair of electrodes B and D, the pair of electrodes A and D, the pair of electrodes A and B, the pair of electrodes C and D and the pair of electrodes C and B are a pair of electrodes to be selected for every electrode group of the electrode pads 4a to 4d.

The pad selector 11a calculates voltages $V_{1A}$, $V_{2A}$, and $V_{3A}$ of the electrode pad 4a based on each piece of digital data of the voltages $V_{11}$, $V_{12}$, $V_{21}$, $V_{22}$, $V_{31}$, and $V_{32}$ acquired from the electrode pad 4a. In this case, the pad selector 11a calculates the voltages $V_{1A}$, $V_{2A}$, and $V_{3A}$ based on the following equations (1), (2), and (3).

$$\text{Voltage value } V_{1A}=(\text{voltage }V_{11}^2+\text{voltage }V_{12}^2)^{1/2} \quad (1)$$

$$\text{Voltage value } V_{2A}=(\text{voltage }V_{21}^2+\text{voltage }V_{22}^2)^{1/2} \quad (2)$$

$$\text{Voltage value } V_{3A}=(\text{voltage }V_{31}^2+\text{voltage }V_{32}^2)^{1/2} \quad (3)$$

In a manner similar to this, the pad selector 11a calculates voltages $V_{1B}$, $V_{2B}$, and $V_{3B}$ of the electrode pad 4b based on each piece of digital data of the voltages $V_{11}$, $V_{12}$, $V_{21}$, $V_{22}$, $V_{31}$, and $V_{32}$ acquired from the electrode pad 4b; calculates voltages $V_{1C}$, $V_{2C}$, and $V_{3C}$ of the electrode pad 4c based on each piece of digital data of the voltages $V_{11}$, $V_{12}$, $V_{21}$, $V_{22}$, $V_{31}$, and $V_{32}$ acquired from the electrode pad 4c; and calculates voltages $V_{1D}$, $V_{2D}$, and $V_{3D}$ of the electrode pad 4d based on each piece of digital data of the voltages $V_{11}$, $V_{12}$, $V_{21}$, $V_{22}$, $V_{31}$, and $V_{32}$ acquired from the electrode pad 4d. In this case, the pad selector 11a calculates the voltages $V_{1B}$, $V_{1C}$, and $V_{1D}$ based on an equation similar to equation (1), respectively; calculates the voltages $V_{2B}$, $V_{2C}$, and $V_{2D}$ based on an equation similar to equation (2), respectively; and calculates the voltages $V_{3B}$, $V_{3C}$, and $V_{3D}$ based on an equation similar to equation (3), respectively.

The pad selector 11a performs comparison processing on the voltages $V_{1A}$, $V_{2A}$, and $V_{3A}$ of the electrode pad 4a, the voltages $V_{1B}$, $V_{2B}$, and $V_{3B}$ of the electrode pad 4b, the voltages $V_{1C}$, $V_{2C}$, and $V_{3C}$ of the electrode pad 4c, and the voltages $V_{1D}$, $V_{2D}$, and $V_{3D}$ of the electrode pad 4d, which are thus calculated, and selects an electrode pad based on a result of the comparison processing. Specifically, the pad selector 11a finds out the highest voltage by the comparison processing among the voltages $V_{1A}$, $V_{2A}$, $V_{3A}$, the voltages $V_{1B}$, $V_{2B}$, $V_{3B}$, the voltages $V_{1C}$, $V_{2C}$, $V_{3C}$, and the voltages $V_{1D}$, $V_{2D}$, $V_{3D}$, and selects an electrode pad corresponding to the found-out highest voltage among the electrode pads 4a to 4d. The electrode pad selected by the pad selector 11a among the electrode pads 4a to 4d is the electrode pad that has detected the voltage required for detection of the position and direction of the capsule endoscope 2 inside the body of the subject K, and specifically is the electrode pad in a position closest to the capsule endoscope 2 inside the subject K.

Figure 6:
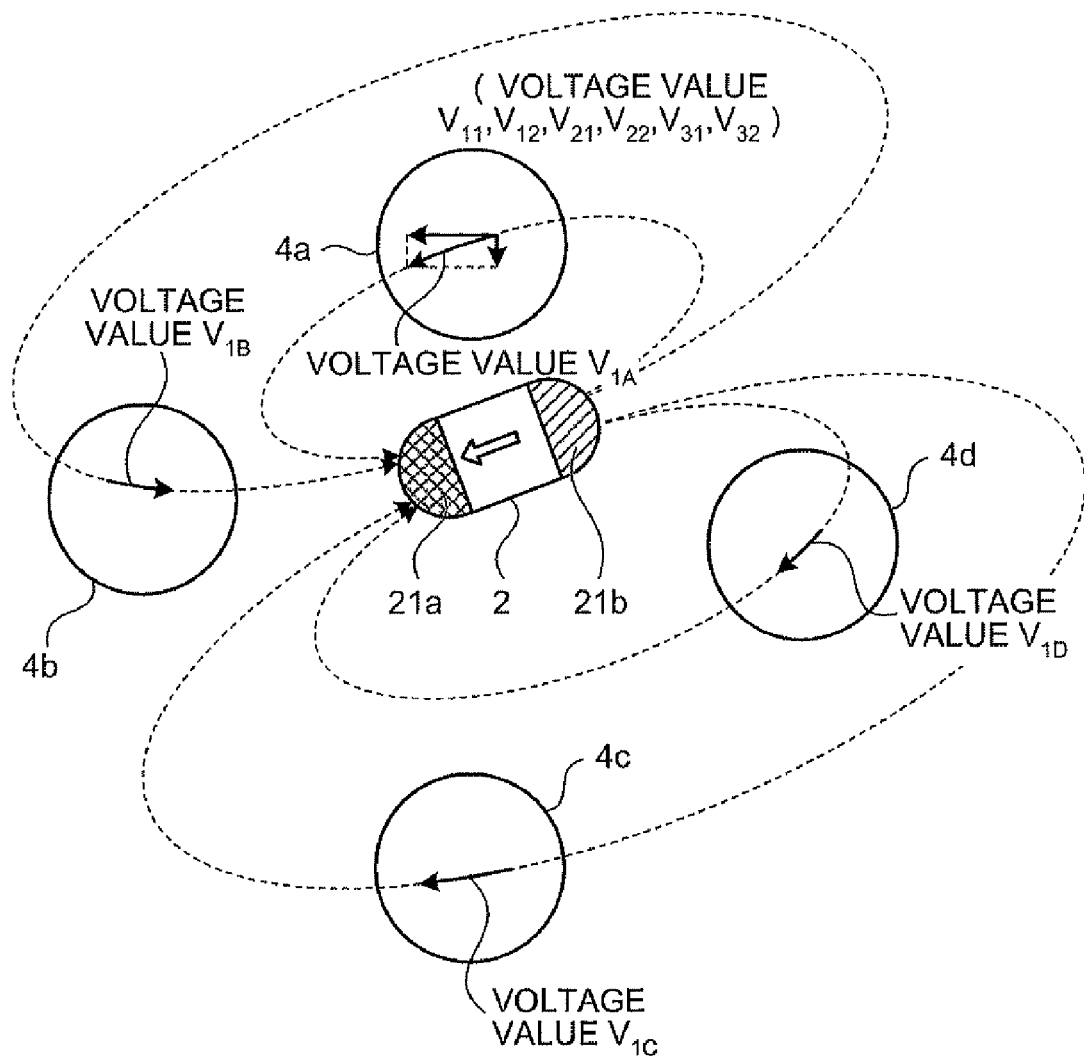
FIG. 6 is a schematic view for illustrating an operation of the position detector for detecting the position and direction of the capsule endoscope inside the body of a subject.

Next, while illustrating a case where the pad selector 11a selects the electrode pad 4a among the electrode pads 4a to 4d, an operation of the position detector 7 for detecting the position and direction of the capsule endoscope 2 inside the body of the subject K will be specifically described. FIG. 6 is a schematic view for illustrating the operations of the position detector 7 for detecting the position and direction of the capsule endoscope 2 inside the body of the subject K.

The position detector 7 acquires from the control unit 11 each piece of digital data of the voltages (voltages $V_{11}$, $V_{12}$, $V_{21}$, $V_{22}$, $V_{31}$, and $V_{32}$) detected by the electrode pad 4a that the pad selector 11a selected, and each piece of position coordinate data of the electrodes A, B, C, and D of the electrode pad 4a. Note herein that each piece of position coordinate data of the electrodes A, B, C, and D is known data that is previously inputted by the input unit 8 and is stored in the storage unit 10. The position detector 7 calculates the position of the capsule endoscope 2 inside the body of the subject K, based on the voltages $V_{11}$, $V_{12}$, $V_{21}$, $V_{22}$, $V_{31}$, and $V_{32}$ acquired as the digital data, and each piece of position coordinate data $(X_A, Y_A, Z_A)$, $(X_B, Y_B, Z_B)$, $(X_C, Y_C, Z_C)$, and $(X_D, Y_D, Z_D)$ of the electrodes A, B, C and D of the electrode pad 4a.

In addition, the position detector 7 calculates the voltages $V_{1A}$, $V_{2A}$, and $V_{3A}$ of the electrode pad 4a based on equations (1), (2), and (3), and finds out the highest voltage among the calculated voltages $V_{1A}$, $V_{2A}$, and $V_{3A}$. Here, if this highest voltage is the voltage $V_{1A}$, a vector direction of this voltage $V_{1A}$ is substantially coincident with a direction of the current produced by the capsule endoscope 2 inside the human body through the human body communications as shown in FIG. 6. The position detector 7 detects a current direction inside the subject K based on the vector direction of the voltage $V_{1A}$, and then detects a direction of the capsule endoscope 2 inside the body of the subject K (refer to a thick line arrow shown in FIG. 6) based on this detected current direction.

When detecting the direction of the capsule endoscope 2 inside the body of the subject K, the position detector 7 may detect the direction of the capsule endoscope 2 using not only the digital data of the detected voltage of the electrode pad that the pad selector 11a selected but also the digital data of the detected voltages of the remaining electrode pads. In other words, the position detector 7 may detect the direction of the capsule endoscope 2 based on the digital data of the detected voltages of all the electrode pads 4a to 4d.

Specifically, the position detector 7 acquires each piece of digital data of the detected voltages (voltages $V_{11}$, $V_{12}$, $V_{21}$, $V_{22}$, $V_{31}$, and $V_{32}$) of all the electrode pads 4a to 4d from the control unit 11, and sequentially calculates the voltages $V_{1A}$, $V_{2A}$, and $V_{3A}$ of the electrode pad 4a, the voltages $V_{1B}$, $V_{2B}$, and $V_{3B}$ of the electrode pad 4b, the voltages $V_{1C}$, $V_{2C}$, and $V_{3C}$ of the electrode pad 4c, and the voltages $V_{1D}$, $V_{2D}$, and $V_{3D}$ of the electrode pad 4d based on equations (1), (2), and (3). The position detector 7 calculates a vector direction of the highest voltage (for example, voltage $V_{1A}$) among the voltages $V_{1A}$, $V_{2A}$, and $V_{3A}$, a vector direction of the highest voltage (for example, voltage $V_{1B}$) among the voltages $V_{1B}$, $V_{2B}$, and $V_{3B}$, a vector direction of the highest voltage (for example, voltage $V_{1C}$) among the voltages $V_{1C}$, $V_{2C}$, and $V_{3C}$, and a vector direction of the highest voltage (for example, voltage $V_{1D}$) among the voltages $V_{1D}$, $V_{2D}$, and $V_{3D}$, respectively.

The vector direction of the highest voltage for every electrode pad is substantially coincident with the direction of the current produced by the capsule endoscope 2 inside the human body through the human body communications as shown in FIG. 6. The position detector 7 detects a current direction in the position of the electrode pad 4a based on the vector direction of the highest voltage $V_{1A}$, detects a current direction in the position of the electrode pad 4b based on the vector direction of the highest voltage $V_{1B}$, detects a current direction in the position of the electrode pad 4c based on the vector direction of the highest voltage $V_{1C}$, and detects a current direction in the position of the electrode pad 4d based on the vector direction of the highest voltage $V_{1D}$. The position detector 7 then detects the direction of the capsule endoscope 2 inside the body of the subject K more accurately based on each current direction thus detected and relative position relations between the electrode pads 4a to 4d. The electrode pads 4a to 4d are provided with four electrodes A to D as the receiving electrode for human body communications, but in order to achieve reception of the image signals that the capsule endoscope 2 inside the subject K transmits by performing the human body communications, and position detection of the capsule endoscope 2 inside the body of the subject, each of the electrode pads 4a to 4d may just be provided with a plurality of electrodes that can form at least a pair of electrodes.

Figure 7:
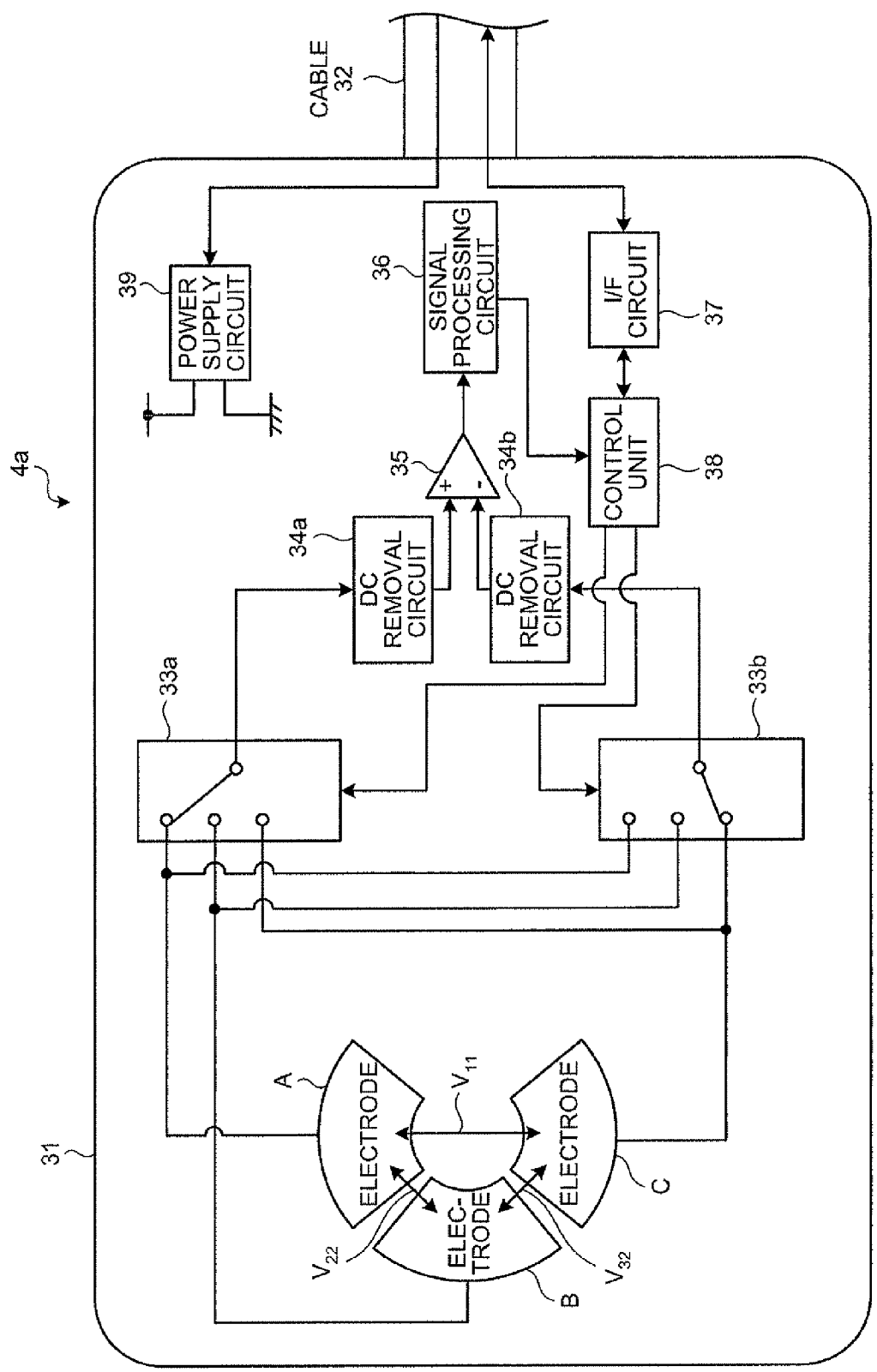
FIG. 7 is a block diagram schematically showing one configuration example of an electrode pad provided with three electrodes as a receiving electrode for human body communications.

Meanwhile, in order to further detect the direction of the capsule endoscope 2 inside the body of the subject K, each of the electrode pads 4a to 4d may just be provided with at least three receiving electrodes. FIG. 7 is a block diagram schematically showing one configuration example of an electrode pad provided with three electrodes as a receiving electrode for human body communications. As shown in FIG. 7, in order to achieve detection of the position and direction of the capsule endoscope 2 inside the body of the subject K, the electrode pad 4a is provided with at least three electrodes A to C. In this case, it is preferable that three electrodes A to C be fixedly arranged so that respective directions of detection voltages may not become parallel to each other, and further preferable that they be fixedly arranged so that angles formed by respective directions of detection voltages may be perpendicular to each other.

Additionally, in the electrode pad 4a, the switching circuits 33a and 33b sequentially select a pair of electrodes among three electrodes A to C, and the signal processing circuit 36 generates each piece of digital data of the voltages $V_{11}$, $V_{22}$, and $V_{32}$ detected by the pair of electrodes among three electrodes A to C. It is to be noted that the remaining electrode pads 4b to 4d have a similar configuration as that of the electrode pad 4a.

Each piece of digital data of the voltages $V_{11}$, $V_{22}$, and $V_{32}$ is transmitted to the communication unit 5 of the receiving apparatus 3 from the I/F circuit 37 via the cable 32 based on the control of the control unit 38. The control unit 11 controls this communication unit 5 to thereby acquire each piece of digital data of the voltages $V_{11}$, $V_{22}$, and $V_{32}$ of the electrode pads 4a to 4d. The position detector 7 acquires from the control unit 11 each piece of digital data of the electrode pad selected among the electrode pads 4a to 4d by the pad selector 11a, and each piece of position coordinate data of the electrodes A to C. The position detector 7 detects the position of the capsule endoscope 2 inside the body of the subject K based on each piece of digital data of the voltages $V_{11}$, $V_{22}$, and $V_{32}$ and each piece of position coordinate data of the electrodes A to C acquired from the control unit 11.

Moreover, the position detector 7 calculates an electric field or a current direction of a displacement current in the position of the electrode pad based on each piece of digital data of the voltages $V_{11}$, $V_{22}$, and $V_{32}$ acquired from the control unit 11, and then detects the direction of the capsule endoscope 2 inside the body of the subject K based on this calculated current direction. In this case, the position detector 7 can calculate a vector direction of a voltage calculated as a square root of an additional value of a square of the voltage $V_{11}$, a square of the voltage $V_{22}$, and a square of the voltage $V_{32}$, and detect the direction of the capsule endoscope 2 based on this calculated vector direction of the voltage. The voltages $V_{11}$, $V_{22}$, and $V_{32}$ used for detecting the direction of the capsule endoscope 2 by the position detector 7 may be the detected voltages of the electrode pad selected by the pad selector 11a among the electrode pads 4a to 4d, or may be the detected voltages of all the electrode pads 4a to 4d. As described above, it is configured in the first embodiment of the present invention such that for every electrode pad fixed to the body surface of the subject, the receiving electrode group which receives the subject information transmitted by the capsule medical device inside the human body through the human body communications is fixedly arranged, and the receiving electrode group is fixedly arranged at the local part, which is within the body surface of the subject, and whose position coordinates is known, and moreover, the A/D conversion processing unit for digital-converting the signals detected by the receiving electrode group is incorporated in the electrode pad, and at least one of the position and direction of the capsule medical device inside the human body is detected based on the digital data of the subject information digital-converted by the A/D conversion processing unit and the position coordinate data of the receiving electrode group. For this reason, the voltage can be reliably induced at a pair of electrodes in the receiving electrode group of the electrode pad by the electric field or displacement current emitted inside the human body when the subject information is transmitted by the capsule medical device inside the human body through the human body communications, and the digital data of the subject information detected by the receiving electrode group through the human body communications can also be transmitted to the external receiving apparatus via the cables. As a result of this, a situation where the voltage is induced at only one receiving electrode in the receiving electrode group on the surface of the human body upon performing the human body communications can be prevented, and the effect of peripheral noise upon data transmission via the cable can also be reduced, thereby making it possible to achieve the capsule medical system and the biological information acquiring method that can reduce the noise of the data of the subject information or the like transmitted through the human body communications.

Using the capsule medical system or the biological information acquiring method in accordance with the first embodiment makes it possible to highly accurately detect the position and direction of the capsule medical device inside the human body, and to also increase reception sensitivity of the subject information such as the image data or the like transmitted by the capsule medical device through the human body communications.

Next, a second embodiment of the present invention will be described. In the first embodiment, a plurality of electrode pads 4a to 4d provided with the receiving electrode group for human body communications are fixedly arranged at local parts, respectively, on the body surface of the subject K, but in this second embodiment, the receiving electrode group for human body communications is fixedly arranged at each local part within a sheet-shaped electrode pad, and the sheet-shaped electrode pad provided with the receiving electrode group at each local part is fixedly arranged onto the body surface of the subject K.

Figure 8:
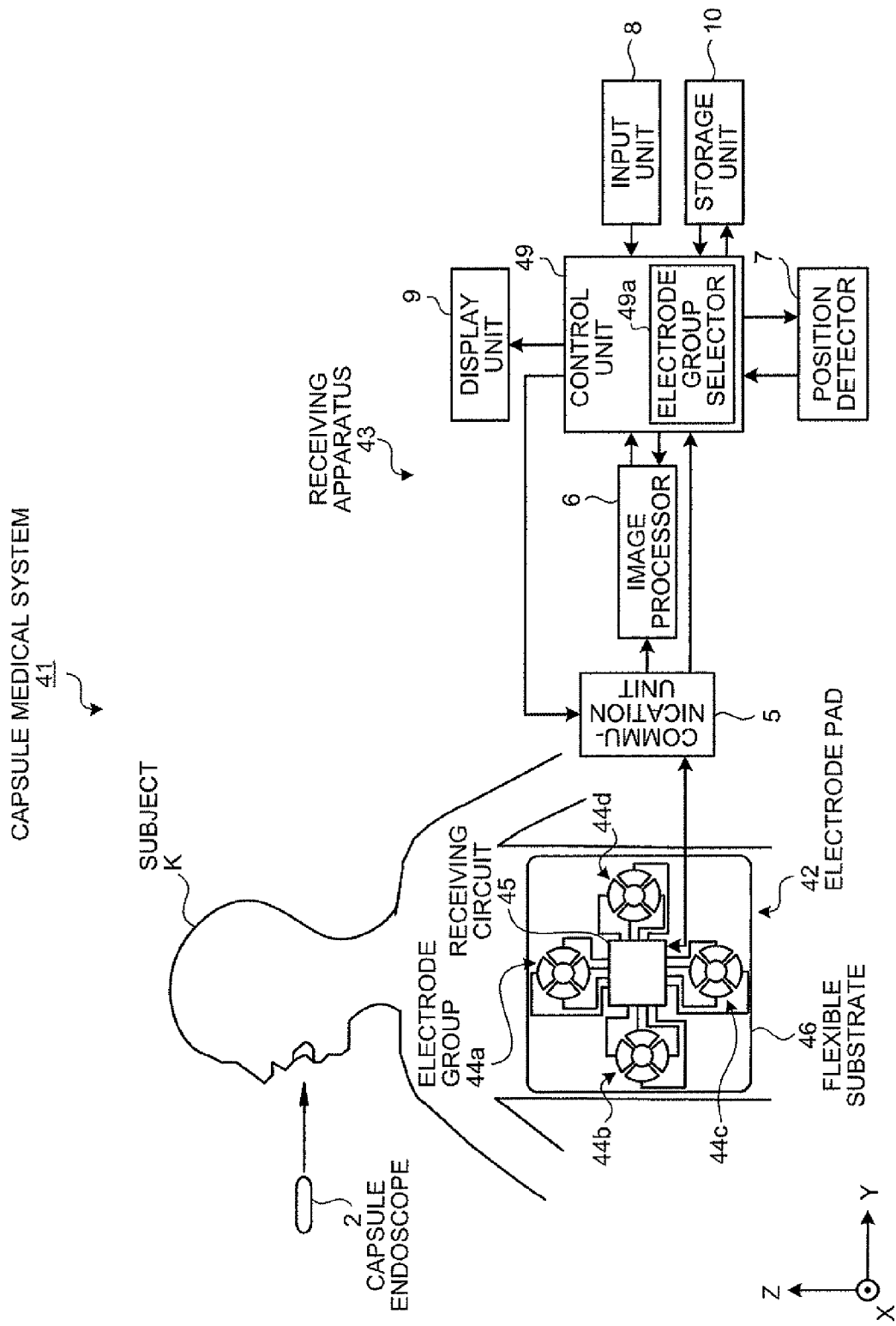
FIG. 8 is a block diagram schematically showing one configuration example of a capsule medical system in accordance with a second embodiment of the present invention.

FIG. 8 is a block diagram schematically showing one configuration example of a capsule medical system in accordance with the second embodiment of the present invention. As shown in FIG. 8, a capsule medical system 41 in accordance with the second embodiment is provided with a receiving apparatus 43 in place of the receiving apparatus 3 of the capsule medical system 1 in accordance with the first embodiment. The receiving apparatus 43 is provided with a sheet-shaped electrode pad 42 in place of the electrode pads 4a to 4d of the receiving apparatus 3 in accordance with the first embodiment, and is provided with a control unit 49 in place of the control unit 11. Other configurations are the same as those of the first embodiment, and the same reference numeral is given to the same configuration.

The electrode pad 42 is a sheet-shaped electrode pad to be pasted onto the body surface of the subject K, and has a plurality of receiving electrode groups for receiving the signals transmitted by the capsule endoscope 2 inside the subject K through the human body communications. Specifically, the electrode pad 42 is provided with a plurality of electrode groups 44a to 44d which are the receiving electrode groups for human body communications, a receiving circuit 45 for receiving the subject information detected by the electrode groups 44a to 44d, and a flexible board 46 for mounting the above electrode groups 44a to 44d and receiving circuit 45, as shown in FIG. 8.

The electrode groups 44a to 44d are the receiving electrode groups for human body communications, wherein they are fixedly arranged at a plurality of local parts within the flexible board 46, respectively, and are also connected with the receiving circuit 45 by a circuit formed in the flexible board 46. When the flexible board 46 is fixedly arranged onto the body surface of the subject K, the electrode groups 44a to 44d are fixedly arranged at a plurality of local parts, which are within the body surface of the subject K, and whose position coordinates are known. The electrode groups 44a to 44d detect the subject information transmitted by the capsule endoscope 2 inside the subject K through the human body communications, and send out the detected subject information to the receiving circuit 45.

The receiving circuit 45 has a switching function of sequentially selecting a pair of electrodes for every electrode group among the electrode groups 44a to 44d, and an A/D conversion processing function of digital-converting the subject information detected by the pair of electrodes. Specifically, the receiving circuit 45 is mounted at a predetermined position of the flexible board 46, and is connected with the electrode groups 44a to 44d by the circuit of this flexible board 46. The receiving circuit 45 is connected with the communication unit 5 of the receiving apparatus 43 through a cable. The receiving circuit 45 receives the subject information detected by the electrode groups 44a to 44d, and digitizes this received subject information to transmit it to the communication unit 5.

The flexible board 46 is a sheet-shaped flexible circuit board in which a circuit required for achieving the aforementioned function of the electrode groups 44a to 44d and function of the receiving circuit 45 is formed, wherein the electrode groups 44a to 44d and the receiving circuit 45 are mounted at predetermined positions thereof. The flexible board 46 connects the electrode groups 44a to 44d with the receiving circuit 45 through the circuit, and also specifies a relative position relation of each electrode included in the electrode groups 44a to 44d. When being fixedly arranged onto the body surface of the subject K, the flexible board 46 fixedly arranges the electrode groups 44a to 44d at a plurality of local parts, which are within the body surface of the subject K, and whose position coordinates are known. As a result, the position and direction of each electrode included in the electrode groups 44a to 44d within the flexible board 46 are fixed to the subject K as the known position coordinate and vector direction in the Cartesian coordinate system XYZ in a manner similar to the case of the first embodiment.

Meanwhile, the control unit 49 of the receiving apparatus 43 sequentially transmits the control signals to the electrode pad 42 through the communication unit 5, and controls the electrode pad 42 by the control signal. In this case, the control unit 49 causes any one of the electrode groups 44a to 44d to detect the image signals transmitted by the capsule endoscope 2 through the human body communications. In other words, the control unit 49 causes a pair of electrodes included in each of the electrode groups 44a to 44d to detect a voltage induced by an electric field or a displacement current produced in the body of the subject K by the capsule endoscope 2 through the human body communications.

Additionally, the control unit 49 is provided with an electrode group selector 49a in place of the pad selector 11a of the receiving apparatus 3 in accordance with the first embodiment. The electrode group selector 49a selects a suitable electrode group for detection processing of the position and direction of the capsule endoscope 2 among the plurality of electrode groups 44a to 44d within the electrode pad 42.

Specifically, the electrode group selector 49a sequentially acquires the digital data of the voltage from the electrode pad 42 via the communication unit 5, and selects among the electrode groups 44a to 44d the suitable electrode group for the detection processing of the position and direction of the capsule endoscope 2, in other words, the electrode group in a position closest to the capsule endoscope 2 inside the subject K, based on each voltage of the acquired digital data. The control unit 49 sends out to the position detector 7 the digital data of the voltage detected by the electrode group selected by the electrode group selector 49a, and the position coordinate data of each electrode included in this selected electrode group. The control unit 49 controls the position detector 7 so as to detect the position and direction of the capsule endoscope 2 inside the subject K based on the sent-out digital data of the voltage and position coordinate data of each electrode. It is to be noted that other functions that the control unit 49 has are the same as those of the control unit 11 of the receiving apparatus 3 in accordance with the first embodiment.

Figure 9:
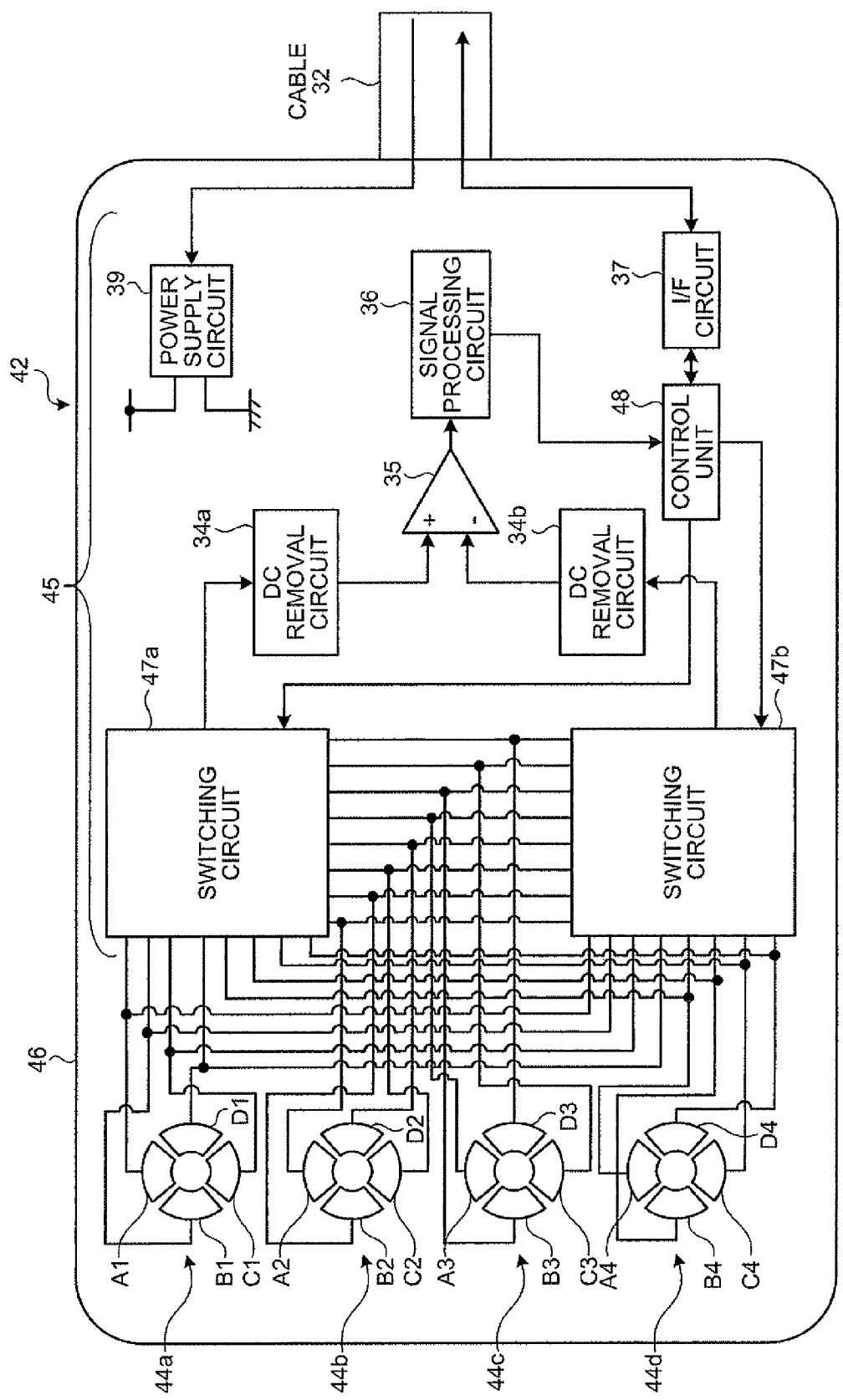
FIG. 9 is a block diagram schematically showing an internal configuration of the electrode pad in accordance with the second embodiment.

Next, a configuration of the electrode pad 42 of the capsule medical system in accordance with the second embodiment of the present invention will be described in detail. FIG. 9 is a block diagram schematically showing an internal configuration of the electrode pad in accordance with the second embodiment. As described above, the electrode pad 42 in accordance with the second embodiment is provided with the plurality of electrode groups 44a to 44d, the receiving circuit 45, and the flexible board 46, and is connected with the communication unit 5 of the receiving apparatus 43 via the cable 32. As shown in FIG. 9 in detail, the electrode group 44a includes four electrodes A1 to D1, the electrode group 44b includes four electrodes A2 to D2, the electrode group 44c includes four electrodes A3 to D3, and the electrode group 44d includes four electrodes A4 to D4. Meanwhile, the receiving circuit 45 is provided with switching circuits 47a and 47b in place of the switching circuits 33a and 33b of the electrode pad in accordance with the first embodiment, and is provided with a control unit 48 in place of the control unit 38. Other configurations are the same as those of the first embodiment, and the same reference numeral is given to the same configuration.

All of the electrodes A1 to D1, A2 to D2, A3 to D3, and A4 to D4 are the receiving electrodes for performing the human body communications with the capsule endoscope 2 inside the human body, and are fixedly arranged in a form of being exposed on the same side of the flexible board 46. The relative position relation and the direction of the electrodes A1 to D1, A2 to D2, A3 to D3, and A4 to D4 are specified by the flexible board 46, and when the electrode pad 42 (specifically, the flexible board 46) is fixedly arranged onto the body surface of the subject K, the electrodes A1 to D1, A2 to D2, A3 to D3, and A4 to D4 are arranged at the fixed position and direction to the subject K, as shown in aforementioned FIG. 8. In this case, the electrodes A1 to D1, A2 to D2, A3 to D3, and A4 to D4 are fixedly arranged at each local parts in the body surface of the subject K, respectively, in a manner similar to that of each electrodes A to D of the electrode pads 4a to 4d in the first embodiment.

Additionally, the electrodes A1 to D1, A2 to D2, A3 to D3, and A4 to D4 detect the image signals from the capsule endoscope 2 by a pair of electrodes for every electrode group, in a manner similar to that of the electrodes A to D in the first embodiment. The image signals that the electrodes A1 to D1, A2 to D2, A3 to D3, and A4 to D4 detected by a pair of electrodes for every electrode group, in other words, the analog data of the voltage induced through the human body communications, are respectively inputted into DC removal circuits 34a and 34k via the switching circuits 47a and 47b.

Although the electrodes A1 to D1, A2 to D2, A3 to D3, and A4 to D4 may be fixedly arranged at desired positions within the flexible board 46 as long as they are in a form of being exposed on the same side of the flexible board 46 and are localized in the local parts within the flexible board 46 for every electrode group, it is preferable to be arranged so that directions perpendicular to each other may be included in each direction of the voltage sequentially detected by a pair of electrodes that are sequentially switched by the switching circuits 47a and 47b for every electrode group.

The switching circuits 47a and 47b are achieved using switching elements, such as a field effect transistor (FET) or the like, and based on control of the control unit 48, sequentially select among each electrodes of the electrode groups 44a to 44d a pair of electrodes that detects the transmission signals from the capsule endoscope 2 through the human body communications for every electrode group. In this case, the switching circuit 47a and the switching circuit 47b neither mutually select the same electrode, nor mutually select the electrodes in different electrode groups. For example, when the switching circuit 47a selects the electrode A1 among the electrodes A1 to D1 in the electrode group 44a, the switching circuit 47b selects any one of the remaining electrodes B1 to D1 included in the same electrode group 44a. The switching circuits 47a and 47b electrically sequentially select among the electrodes A1 to D1, A2 to D2, A3 to D3, and A4 to D4 a pair of electrodes that detects the image signals transmitted by the capsule endoscope 2 through the human body communications, with respect to each of the electrode groups 44a to 44d, and the switching circuit 47a sends out the analog data from one electrode of the selected pair of electrodes to the DC removal circuit 34a, while the switching circuit 47b sends out the analog data from the other electrode to the DC removal circuit 34b.

The control unit 48 controls each component part of the electrode pad 42. Specifically, the control unit 48 controls each switching operation of the switching circuits 47a and 47b, which select a pair of electrodes among the electrode groups 44a to 44d for every electrode group, and also controls input and output of signals between respective component parts of the electrode pad 42. When receiving the control signal from the control unit 49 of the receiving apparatus 43 via the I/F circuit 37, the control unit 48 selects a pair of electrodes among the electrode groups 44a to 44d for every electrode group, and also controls the switching circuits 47a and 47b so as to sequentially switch a pair of electrodes at a predetermined interval, based on this control signal. In this case, the control unit 48 controls the switching operation of the switching circuits 47a and 47b so that the switching circuit 47a and the switching circuit 47b may neither select the same electrode nor select the electrodes of the different electrode groups, simultaneously. It is to be noted that other functions that the control unit 48 has are the same as those of the control unit 38 of the electrode pad in accordance with the first embodiment.

Next, a procedure of the control unit 49 that causes the position detector 7 to detect the position and direction of the capsule endoscope 2 inside the body of the subject K, in the receiving apparatus 43 outside the subject K will be described. The control unit 49 of the receiving apparatus 43 repeatedly performs a procedure almost similar to that of Steps S101 to S105 (refer to FIG. 5) as required to thereby cause the position detector 7 to detect the position and direction of the capsule endoscope 2 inside the body of the subject K.

In this case, the control unit 49 sequentially transmits the control signals to the electrode pad 42 via the communication unit 5 at Step S101 to thereby cause the electrode pad 42 to sequentially select a pair of electrodes among the electrodes A1 to D1, A2 to D2, A3 to D3, and A4 to D4 for every electrode group. Additionally, the control unit 49 selects among all the electrode groups 44a to 44d an electrode group that detected a voltage required for detection of the position and direction of the capsule endoscope 2 at Step S104. In this case, based on all the digital data of the voltage acquired from the electrode pad 42, the electrode group selector 49a performs arithmetic processing in a manner similar to that of a case where the pad selector 11a of the receiving apparatus 3 in accordance with the first embodiment selected the electrode pad, and selects an electrode group corresponding to the highest voltage, in other words, an electrode group in a position closest to the capsule endoscope 2 inside the subject K.

At Step S105, the control unit 49 sends out digital data of each voltage detected for every pair of electrodes by the electrode group that is selected among the electrode groups 44a to 44d by the electrode group selector 49a, and the position coordinate data of the electrode group, to the position detector 7, and also causes the position detector 7 to calculate the position and direction of the capsule endoscope 2 inside the body of the subject K based on these digital data of each voltage and position coordinate data of the electrode group.

The electrode groups 44a to 44d included four electrodes A1 to D1, A2 to D2, A3 to D3, and A4 to D4 as the receiving electrode for human body communications, but in order to achieve the reception of the image signals that the capsule endoscope 2 inside the subject K transmits by performing the human body communications, and the position detection of the capsule endoscope 2 inside the body of the subject, each of the electrode pads 44a to 44d may just include a plurality of electrodes that can form at least a pair of electrodes.

Additionally, in order to further detect the direction of the capsule endoscope 2 inside the body of the subject K, each of the electrode groups 44a to 44d may just be provided with at least three receiving electrodes as shown in FIG. 7. In this case, it is preferable that three receiving electrodes included in each of the electrode groups 44a to 44d be fixedly arranged so that respective directions of detection voltages may not become in parallel to each other, and further preferable that they be fixedly arranged so that angles formed by respective directions of detecting voltages may be perpendicular to each other.

As described above, in the second embodiment of the present invention, the plurality of receiving electrode groups that receive the subject information transmitted by the capsule medical device inside the human body through the human body communications are fixedly arranged at desired local parts within the flexible circuit board forming the outer shape of the electrode pad (sheet shape) to be fixed to the body surface of the subject, and this flexible circuit board is fixedly arranged onto the body surface of the subject, so that the plurality of receiving electrode groups are fixedly arranged at the plurality of local parts, which are within the body surface of the subject, and whose position coordinates are known, respectively. Other configurations are made in a manner similar to those of the first embodiment. For this reason, operation effects similar to those of the first embodiment can be obtained, and the plurality of receiving electrode groups for human body communications can also be easily fixedly arranged at the plurality of local parts, which are within the body surface of the subject, and whose position coordinates are known, thus allowing the position and direction of each electrode in the plurality of receiving electrode groups to be easily fixed to the subject.

Moreover, since the plurality of receiving electrode groups, and the receiving circuit common to the plurality of receiving electrode groups are assembled on the flexible circuit board of the single electrode pad, the number of components of the receiving circuit having the switching function of sequentially selecting a pair of electrodes for every electrode group among the plurality of receiving electrode groups, and the A/D conversion processing function of digital-converting the subject information detected by the pair of electrodes can be reduced, thereby making it possible to simplify the configuration of the electrode pad provided with the receiving electrode groups for human body communications.

Next, a third embodiment of the present invention will be described. In the first embodiment, the position and direction of the capsule endoscope 2 inside the subject K are detected by acquiring the digital data of the voltages detected by the electrode pads 4a to 4d fixedly arranged onto the body surface of the subject K. In the third embodiment, biological activity information, such as heart beats or the like, of the subject K is further detected, and the position and direction of the capsule endoscope 2 is to be detected at a timing when variation of this detected biological activity information is small.

Figure 10:
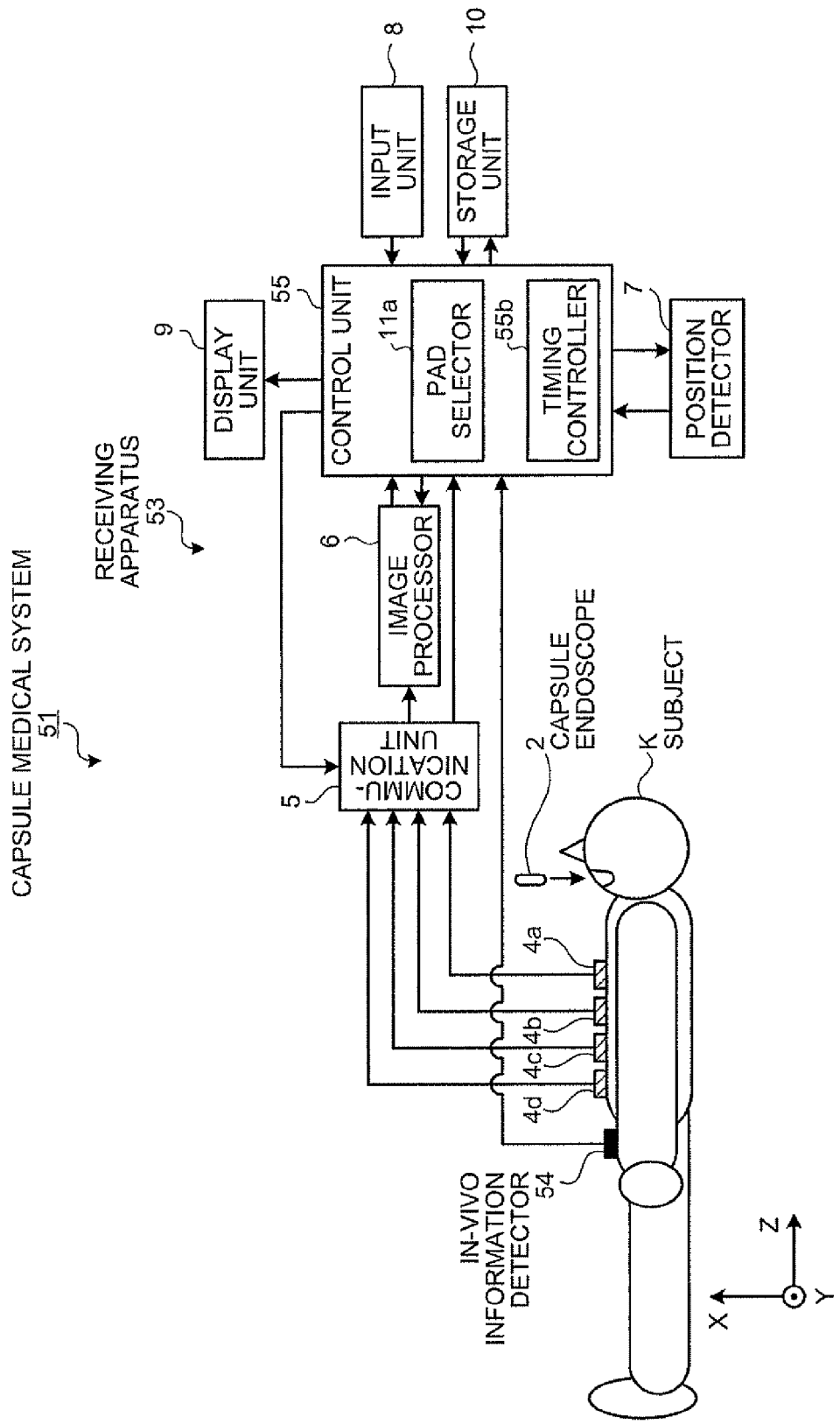
FIG. 10 is a block diagram schematically showing one configuration example of a capsule medical system in accordance with a third embodiment of the present invention.

FIG. 10 is a block diagram schematically showing one configuration example of a capsule medical system in accordance with the third embodiment of the present invention. As shown in FIG. 10, the capsule medical system 51 in accordance with the third embodiment is provided with a receiving apparatus 53 in place of the receiving apparatus 3 of the capsule medical system 1 in accordance with the first embodiment. The receiving apparatus 53 is provided with a control unit 55 in place of the control unit 11 of receiving apparatus 3 in the first embodiment, and is further provided with a biological information detector 54 for detecting biological activity information of the subject K that inserted the capsule endoscope 2 into its body other configurations are the same as those of the first embodiment, and the same reference numeral is given to the same configuration.

The biological information detector 54 is attached to the body surfaces of the subject K (for example, arm of the subject K, or the like), and detects the biological activity information of the subject K in a state of contacting to the body surface of this subject K. The biological information detector 54 sends out the detected biological activity information of the subject K to the control unit 55 of the receiving apparatus 53. The biological activity information of the subject K detected by the biological information detector 54 includes heart beat, blood pressure, blood stream, breathing, body temperature, biological impedance, or the like of the subject K, for example.

The control unit 55 controls the biological information detector 54. Additionally, the control unit 55 has a timing controller 55b for controlling a timing to cause the position detector 7 to detect the position and direction of the capsule endoscope 2 inside the subject K. Other functions that the control unit 55 has are similar to those of the control unit 11 of the receiving apparatus 3 in accordance with the first embodiment.

The timing controller 55b controls the timing to cause the position detector 7 to detect the position and direction of the capsule endoscope 2 inside the subject K based on the biological activity information of the subject K detected by the biological information detector 54. Specifically, the timing controller 55b sequentially acquires the biological activity information of the subject K detected by the biological information detector 54, and calculates variation of this acquired biological activity information each time. The timing controller 55b performs comparison processing between this calculated variation of the biological activity information and a predetermined threshold value previously set, and based on this comparison processing result, it grasps a period while the variation of the biological activity information of the subject K is the threshold value or less (i.e., a period while the variation of the biological activity information of the subject K is small). The timing controller 55b sequentially acquires the digital data of the voltages detected by the electrode pads 4a to 4d during the period while the variation of the biological activity information is small, via the communication unit 5, and controls the position detector 7 so as to detect the position and direction of the capsule endoscope 2 using the digital data of the voltage detected during this period. Thus, the timing controller 55b causes the position detector 7 to detect the position and direction of the capsule endoscope 2 inside the subject K at the timing when the variation of the biological activity information of the subject K is small.

The digital data to be sent out to the position detector 7 whose timing to detect the position and direction of the capsule endoscope 2 is controlled by the timing controller 55b is the digital data of the voltage detected during the period while the variation of the biological activity information of the subject K is the threshold value or less, and is the digital data of the voltage detected by the electrode pad that the pad selector 11a selected among the electrode pads 4a to 4d.

Next, a procedure of the control unit 55 for causing the position detector 7 to detect the position and direction of the capsule endoscope 2 inside the body of the subject K, in the receiving apparatus 53 outside the subject K will be described. The control unit 55 of the receiving apparatus 53 repeatedly performs a procedure almost similar to that of Steps S101 to S105 (refer to FIG. 5) as required to thereby cause the position detector 7 to detect the position and direction of the capsule endoscope 2 inside the body of the subject K.

In this case, the timing controller 55b first performs, at Step S102, the comparison processing between the variation of the biological activity information of the subject K detected by the biological information detector 54, and the predetermined threshold value, and determines whether or not this variation of the biological activity information is the threshold value or less, in other words, whether or not it is a period while the variation of the biological activity information of the subject K is a small. Subsequently, the timing controller 55b acquires the digital data of the voltages from the electrode pads 4a to 4d, when it is the period while the variation of the biological activity information is small.

Meanwhile, at Step S105, the timing controller 55b controls the position detector 7 to detect the position and direction of the capsule endoscope 2 inside the body of the subject K, based on the digital data of the voltage detected during the period while the variation of the biological activity information of the subject K is the threshold value or less and also the digital data of the voltage detected by the electrode pad that the pad selector 11a selected, and the position coordinate data of the electrode group of this electrode pad.

Figure 11:
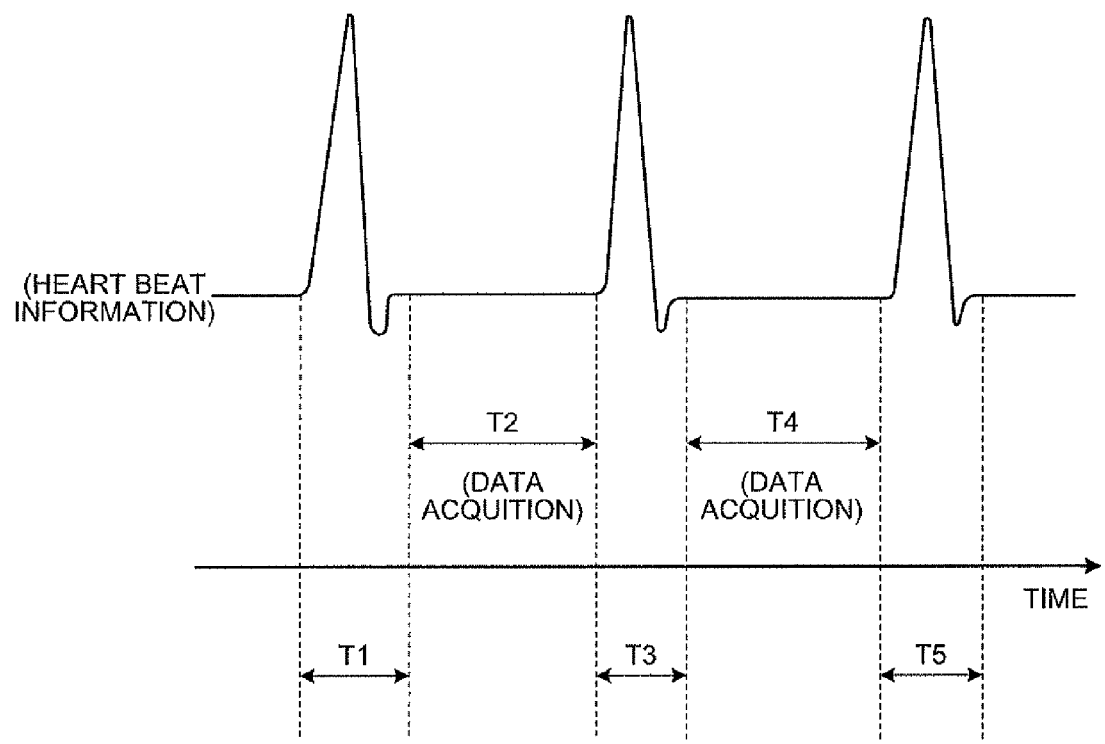
FIG. 11 is a schematic view illustrating an acquisition timing of digital data of voltages.

Next, while exemplifying the heart beat, which is one example of the biological activity information of the subject K, detected by the biological information detector 54, acquisition timing of the digital data of the voltages detected by the electrode pads 4a to 4d will be described. FIG. 11 is a schematic view illustrating the acquisition timing of the digital data of the voltages.

As shown in FIG. 11, the biological information detector 54 detects heart beat information as the biological activity information of the subject K, and sends out this detected heart beat information to the control unit 55. In this case, the timing controller 55b calculates the variation of the heart beat information acquired from the biological information detector 54, performs comparison processing between the calculated variation of the heart beat information and a predetermined threshold value, and grasps a period while this variation of the heart beat information is the threshold value or less, in other words, a period while the variation of the heart beat information is small. The timing controller 55b grasps, for example, periods T2 and T4 while the variation of the heart beat information is small, among continuous periods T1 to T5, and sequentially acquires the digital data of the voltages that the electrode pads 4a to 4d detected during the periods T2 and T4.

The voltage induced between a pair of electrode pads when the electrode pads 4a to 4d detect the image signals transmitted by the capsule endoscope 2 inside the subject K through the human body communications varies with the variation of the biological activity information of the subject K exemplified by the heart beat information to thereby cause an error in the detection voltage of the electrode pads 4a to 4d. As a result of this, an error may be caused in a detection result of the position and direction of the capsule endoscope 2 detected by the position detector 7.

In contrast with this, the timing controller 55b sequentially acquires the digital data of the voltages detected by the electrode pads 4a to 4d, via the communication unit 5 during the period while the variation of the biological activity information of the subject K is small (for example, periods T2 and T4 shown in FIG. 11), and controls the position detector 7 so as to detect the position and direction of the capsule endoscope 2 using the digital data. Consequently, the timing controller 55b can suppress the variation of the digital data of the voltage caused by the variation of the biological activity information of the subject K, and can also reduce the error in the detection result of the position and direction of the capsule endoscope 2 that the position detector 7 is caused to detect.

The timing controller 55b may delete the digital data of the voltages outputted from the electrode pads 4a to 4d during the period while the variation of the biological activity information of the subject K exceeds the threshold value, namely, the period while the variation of the biological activity information of the subject K is large (for example, periods T1, T3, and T5 shown in FIG. 11), or may add a flag or the like to the digital data acquired during the period while the variation of the biological activity information is large to distinguish it from other digital data of the voltage (digital data acquired during the period while the variation of the biological activity information is small).

As described above, in the third embodiment of the present invention, the biological information detector for detecting the biological activity information of the subject into which the capsule medical device is inserted is further arranged onto the body surface of the subject; the position and direction of the capsule endoscope inside the subject are detected at the timing when the variation of the biological activity information detected by the biological information detector is small. Other configurations are made in a manner similar to the first embodiment. For this reason, operation effects similar to those of the first embodiment can be obtained, and the error caused in the detection voltage of the electrode pad due to the variation of the biological activity information of the subject can also be reduced, thus allowing detection accuracy of the position and direction of the capsule medical device inside the body of the subject to be increased.

Next, a fourth embodiment of the present invention will be described. In the third embodiment, the electrode pads 4a to 4d provided with the receiving electrode group for human body communications, and the biological information detector 54 are fixedly arranged onto the body surface of the subject K (pasted onto the body surface), while in this fourth embodiment, the electrode pads 4a to 4d and the biological information detector 54 are fixedly arranged onto a supporting surface for supporting the subject K, and the electrode pads 4a to 4d and the biological information detector 54 are fixedly contacted to the body surface of the subject K by contacting the body surface of the subject K to this supporting surface.

Figure 12:
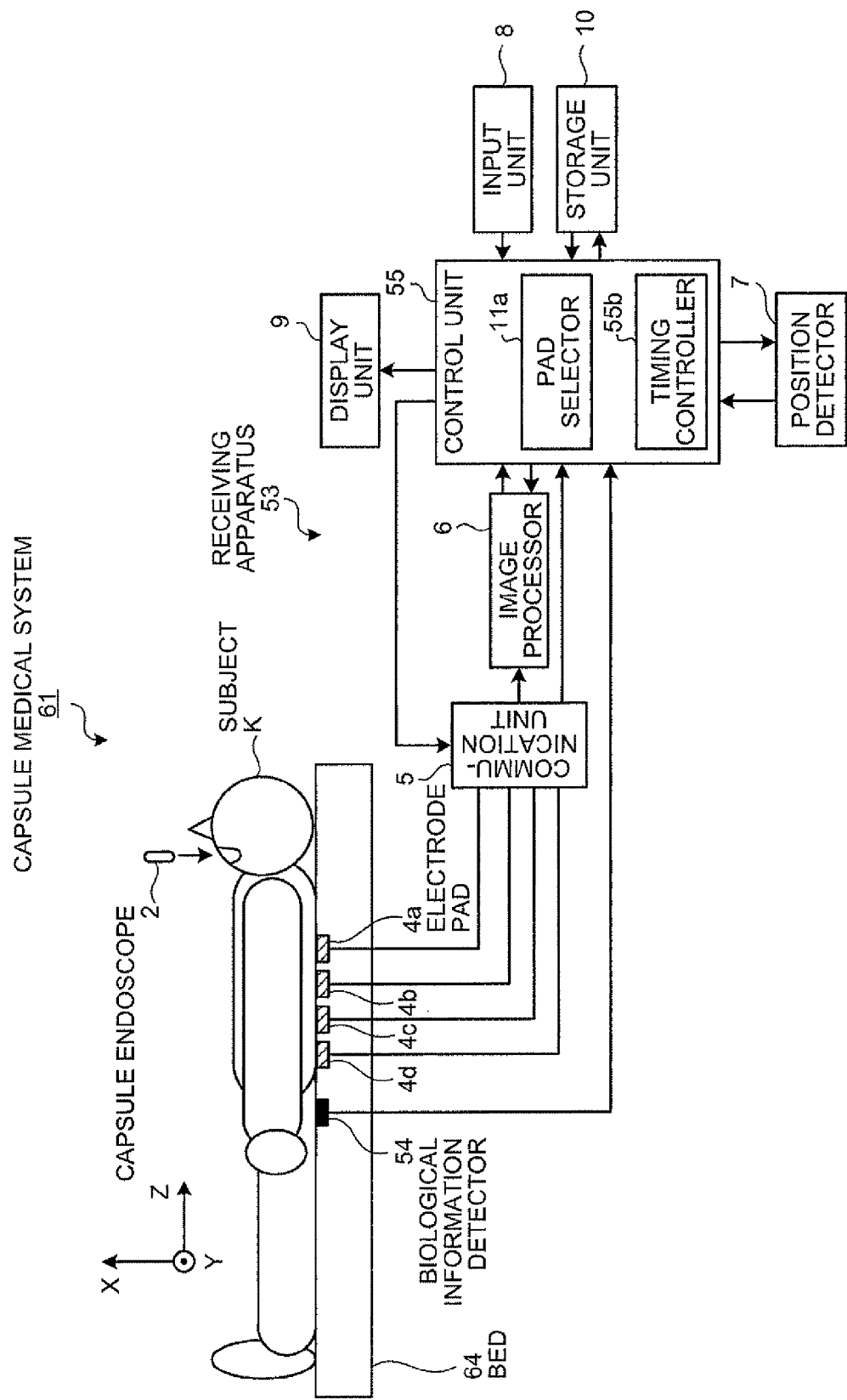
FIG. 12 is a block diagram schematically showing one configuration example of a capsule medical system in accordance with a fourth embodiment of the present invention.

FIG. 12 is a block diagram schematically showing one configuration example of a capsule medical system in accordance with the fourth embodiment of the present invention. As shown in FIG. 12, a capsule medical system 61 in accordance with this fourth embodiment is further provided with a bed 64 for supporting the subject K. The electrode pads 4a to 4d and the biological information detector 54 of the receiving apparatus 53 are fixedly arranged onto a subject supporting surface of the bed 64. The electrode pads 4a to 4d and the biological information detector 54 arranged onto the subject supporting surface fixedly contact to this body surface of the subject K by making the bed 64 support (mount) the subject K. Other configurations are the same as those of the third embodiment, and the same reference numeral is given to the same configuration.

The bed 64 is one example of the supporting member for supporting the subject K into which the capsule endoscope 2 is inserted. The electrode pads 4a to 4d and the biological information detector 54 are fixedly arranged onto the subject supporting surface of the bed 64. In this case, the electrode pads 4a to 4d are fixedly arranged respectively at each local parts, which are within the subject supporting surface of the bed 64, and whose position coordinates are known, in the form of being exposed from this subject supporting surface. In other words, the bed 64 specifies a relative position relation of each electrode included in the electrode pads 4a to 4d, which are fixedly arranged onto this subject supporting surface, in a manner almost similar to that of the flexible board 46 of the electrode pad 42 in accordance with the second embodiment. By supporting the subject K to that subject supporting surface, the bed 64 fixedly contacts each electrode of the electrode pads 4a to 4d to a plurality of local parts, which are within the body surface of the subject, and whose position coordinates are known. As a result, the position and direction of each electrode included in the electrode pads 4a to 4d are fixed to this subject K as the known position coordinate and vector direction in the Cartesian coordinate system XYZ.

Additionally, by supporting the subject K to the subject supporting surface, the bed 64 contacts the electrode pads 4a to 4d and the body surface of the subject K to each other, and simultaneously, fixedly contacts the biological information detector 54 to a predetermined position within the body surface of the subject. As a result, the biological information detector 54 will be in a state of being able to detect the biological activity information of the subject K.

As described above, in the fourth embodiment of the present invention, the biological information detector for detecting the biological activity information of the subject, and the electrode pad for detecting the subject information transmitted by the capsule medical device through the human body communications are fixedly arranged onto the subject supporting surface of the supporting member for supporting the subject into which the capsule medical device is inserted, and the subject supporting surface of this supporting member is made to support the subject (mount), so that the receiving electrode group of the electrode pad and the biological information detector are fixedly contacted to the body surface of the subject. Other configurations are made in a manner similar to the third embodiment. For this reason, operation effects similar to those of the third embodiment can be obtained, and the receiving electrode group of the electrode pad and the biological information detector can also be fixedly contacted to the body surface of the subject without fixedly arranging the electrode pad and the biological information detector onto the body surface of the subject by pasting or the like, thus allowing discomfort upon fixedly arranging the electrode pad or the biological information detector onto the subject to be reduced.

Next, a fifth embodiment of the present invention will be described. In the first embodiment, the position and direction of the capsule endoscope 2 inside the subject K are detected by acquiring the digital data of the voltages detected by the electrode pads 4a to 4d fixedly arranged onto the body surface of the subject K. In the fifth embodiment, displacement of the electrode pads 4a to 4d on the body surface displaced with the biological activities, such as breathing or the like of the subject K is further detected, and the position coordinate data of the electrode group of the electrode pads 4a to 4d is corrected based on this detected displacement of the electrode pads 4a to 4d.

Figure 13:
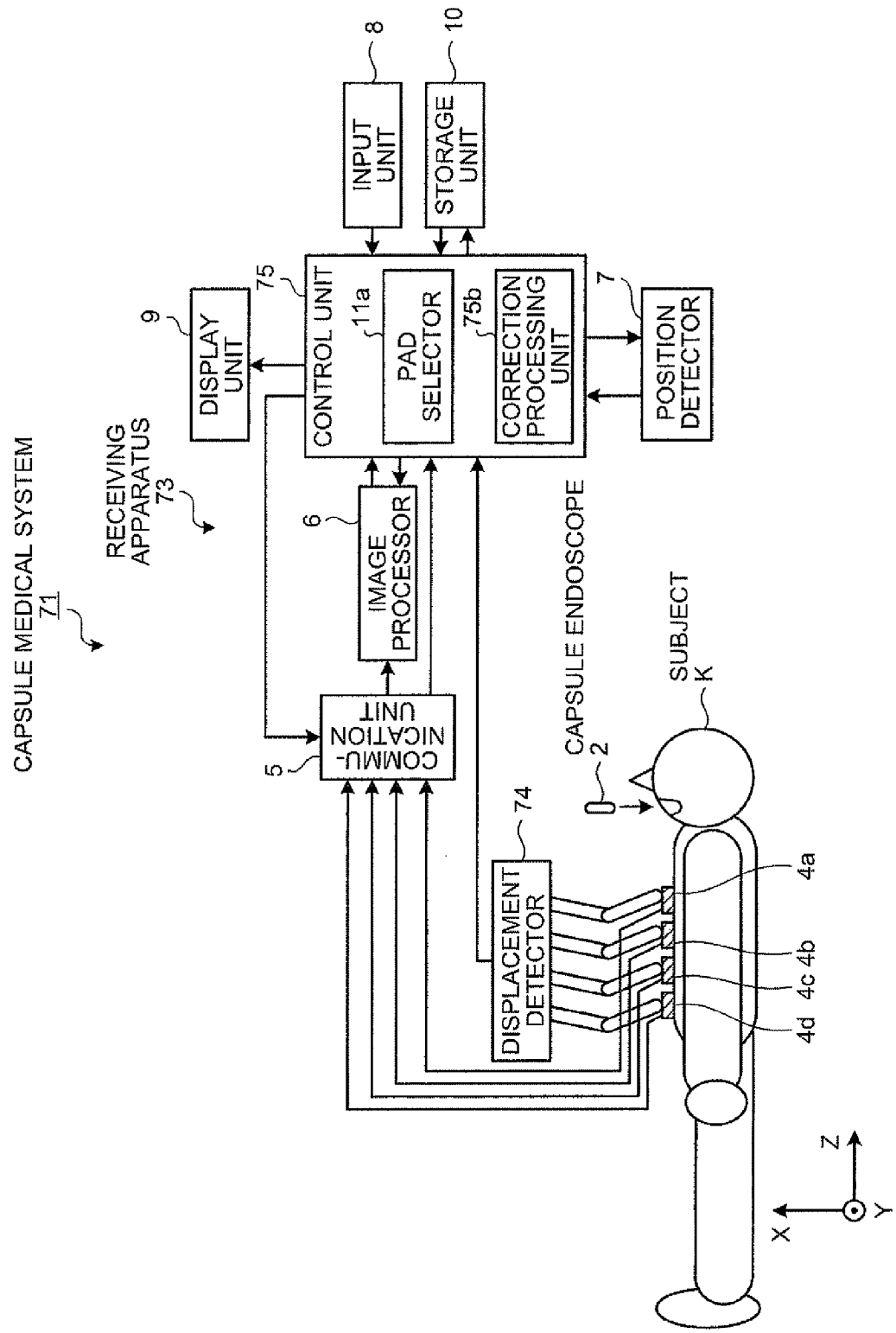
FIG. 13 is a block diagram schematically showing one configuration example of a capsule medical system in accordance with a fifth embodiment of the present invention.

FIG. 13 is a block diagram schematically showing one configuration example of a capsule medical system in accordance with the fifth embodiment of the present invention. As shown in FIG. 13, a capsule medical system 71 in accordance with the fifth embodiment is provided with a receiving apparatus 73 in place of the receiving apparatus 3 of the capsule medical system 1 in accordance with the first embodiment. The receiving apparatus 73 is provided with a control unit 75 in place of the control unit 11 of the receiving apparatus 3 of the first embodiment, and is further provided with a displacement detector 74 for detecting the displacement of the electrode pads 4a to 4d fixedly arranged onto the body surface of the subject K. Other configurations are the same as those of the first embodiment, and the same reference numeral is given to the same configuration.

The displacement detector 74 detects the displacement of the electrode pads 4a to 4d displaced with the body surface in connection with the biological activities, such as breathing or the like of the subject K, for every electrode pad, in the Cartesian coordinate system XYZ. Specifically, the displacement detector 74 has movable arms for operating with the displacement of the electrode pads 4a to 4d while respectively contacting to the electrode pads 4a to 4d on the body surface of the subject K, and mechanically detects each displacement of the electrode pads 4a to 4d based on the operations of the movable arms. The displacement detector 74 sends out each displacement detection result of the electrode pads 4a to 4d thus detected to the control unit 75 as displacement information. The displacement information detected by the displacement detector 74 includes each amount of displacement and each displacement direction of the electrode pads 4a to 4d displaced in connection with the biological activities of the subject K.

Note herein that, the displacement detector 74 detects the displacement of the electrode pads 4a to 4d while contacting the movable arms to the electrode pads 4a to 4d on the body surface of the subject K, but not limited thereto. The displacement detector 74 may detect displacement of the body surface displaced with the biological activities of the subject K while contacting the movable arms to the body surface of the subject K (for example, each vicinity of the electrode pads 4a to 4d) to thereby detect each displacement of the electrode pads 4a to 4d based on the detected displacement of the body surface. Meanwhile, the displacement detector 74 may be integrally arranged with the bed 64 for supporting the subject K as described above.

The control unit 75 controls the displacement detector 74 in place of the biological information detector 54. Additionally, the control unit 75 has a correction processing unit 75b for correcting the position coordinate data of each electrode of the electrode pads 4a to 4d based on the displacement information of the electrode pads 4a to 4d in place of the timing controller 55b. Other functions that the control unit 75 has are similar to those of the control unit 11 of the receiving apparatus 3 in accordance with the first embodiment.

The correction processing unit 75b corrects the position coordinate data of each electrode of the electrode pads 4a to 4d based on the displacement of the electrode pads 4a to 4d detected by the displacement detector 74. Specifically, the control unit 75 sequentially acquires each piece of displacement information of the electrode pads 4a to 4d detected by the displacement detector 74. In this case, the correction processing unit 75b reads each piece of position coordinate data of the electrode group of the electrode pads 4a to 4d from the storage unit 10, and performs compensation processing on each piece of position coordinate data of the electrode group of the electrode pads 4a to 4d for every electrode based on each piece of displacement information of the electrode pads 4a to 4d acquired from the displacement detector 74. By the compensation processing of the correction processing unit 75b, each piece of position coordinate data of the electrode group of the electrode pads 4a to 4d is corrected to data to which the displacement of the electrode pads 4a to 4d resulting from the biological activities of the subject K is added. The control unit 75 controls the position detector 7 so as to detect the position and direction of the capsule endoscope 2 inside the body of the subject K using each piece of position coordinate data of the electrode group of the electrode pads 4a to 4d, on which the compensation processing is performed by the correction processing unit 75b, and the aforementioned digital data of the voltage.

Next, a procedure of the control unit 75 for causing the position detector 7 to detect the position and direction of the capsule endoscope 2 inside the body of the subject K, in the receiving apparatus 73 outside the subject K will be described. The control unit 75 of the receiving apparatus 73 repeatedly performs a procedure almost similar to that of Steps S101 through S105 (refer to FIG. 5) as required to thereby cause the position detector 7 to detect the position and direction of the capsule endoscope 2 inside the body of the subject K.

In this case, the correction processing unit 75b corrects each piece of position coordinate data of the electrode group of the electrode pads 4a to 4d for every electrode based on the displacement information of the electrode pads 4a to 4d acquired from the displacement detector 74 at Step S105. The control unit 75 controls the position detector 7 so as to detect the position and direction of the capsule endoscope 2 inside the body of the subject K using the digital data of the voltage detected by the electrode pad that are selected by the pad selector 11a, and the position coordinate data corrected by the correction processing unit 75b.

As described above, in the fifth embodiment of the present invention, the displacement detector for detecting the displacement information of the electrode pad for human body communications fixedly arranged onto the body surface of the subject is further arranged, the displacement information of the electrode pad on the body surface displaced in connection with the biological activities of the subject is detected, the compensation processing of the position coordinate data of the electrode group of this electrode pad is performed based on the detected displacement information of the electrode pad, the position and direction of the capsule medical device inside the body of the subject are detected based on the position coordinate data on which the compensation processing is performed, and the digital data of the detection voltage by the electrode pad, and other configurations are made in a manner similar to the first embodiment. For this reason, operation effects similar to those of the first embodiment can be obtained, and the position coordinate data of the electrode group fixedly arranged at the local part, which is within the body surface of the subject, and whose position coordinate is known, can also be compensation-processed into the actual position coordinate data of the electrode group displaced with the body surface in connection with the biological activities of the subject, thus allowing detection accuracy of the position and direction of the capsule medical device inside the body of the subject to be increased.

Next, a sixth embodiment of the present invention will be described. In the aforementioned fifth embodiment, the displacement of the electrode pads 4a to 4d is mechanically detected by the displacement detector 74 having the movable arms, which operate with the electrode pads 4a to 4d in connection with the biological activities of the subject K, while in the sixth embodiment, the displacement of the electrode pads 4a to 4d is detected by magnetic sensors by providing magnetic substances, such as a magnet and the like to the electrode pads 4a to 4d.

Figure 14:
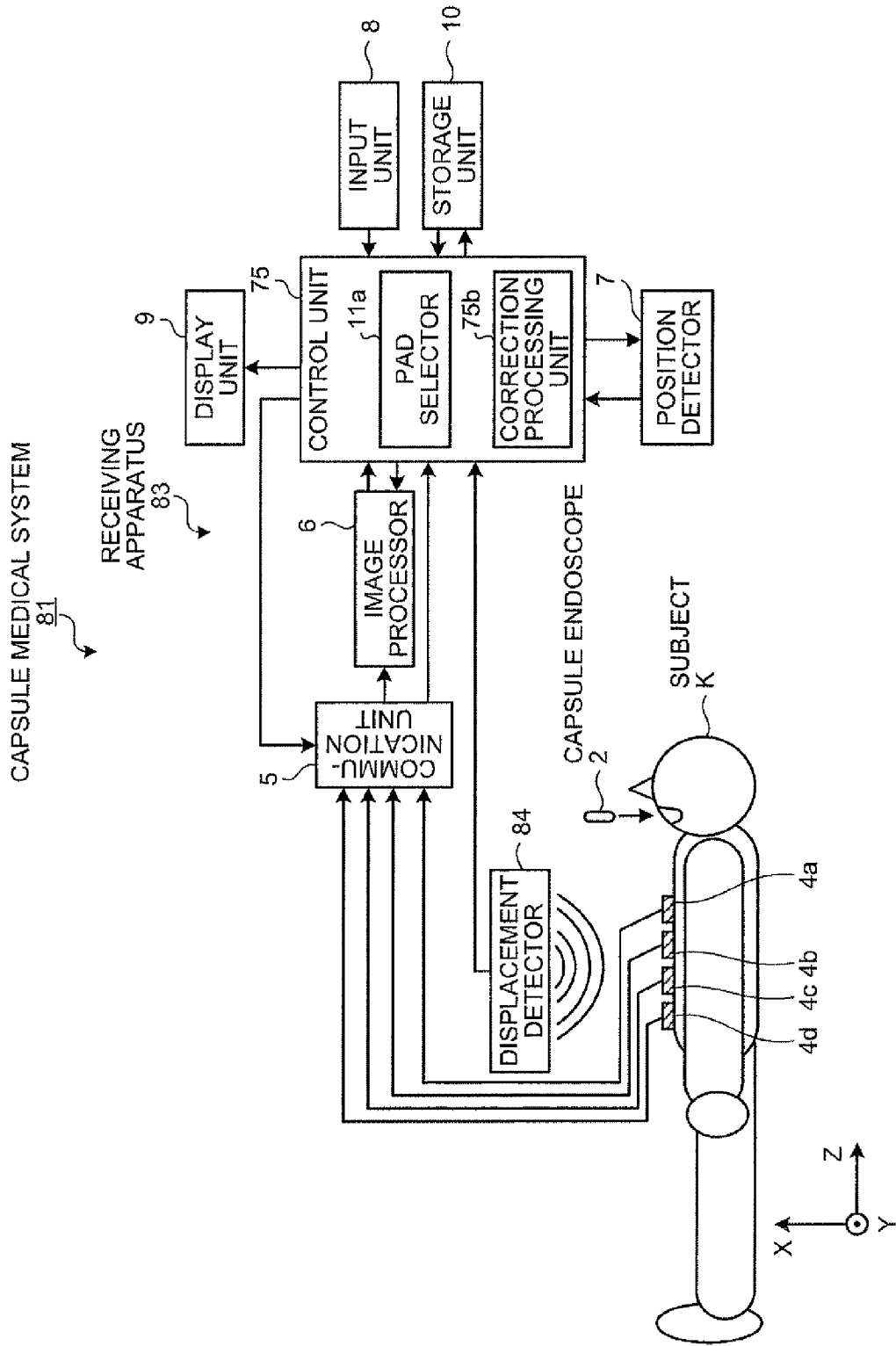
FIG. 14 is a block diagram schematically showing one configuration example of a capsule medical system in accordance with a sixth embodiment of the present invention.

FIG. 14 is a block diagram schematically showing one configuration example of a capsule medical system in accordance with the sixth embodiment of the present invention. As shown in FIG. 14, a capsule medical system 81 in accordance with the sixth embodiment is provided with a receiving apparatus 83 in place of the receiving apparatus 73 of the capsule medical system 71 in accordance with the fifth embodiment. The receiving apparatus 83 is provided with a displacement detector 84 in place of the displacement detector 74 of the receiving apparatus 73 of the fifth embodiment. It is to be noted that although not shown particularly, a magnetic substance (one example of a physical quantity generation unit for generating magnetism as physical quantity), such as a permanent magnet or the like, is provided to each of the electrode pads 4a to 4d in the sixth embodiment. Other configurations are the same as those of the fifth embodiment, and the same reference numeral is given to the same configuration.

The displacement detector 84 detects the displacement of the electrode pads 4a to 4d displaced with the body surface in connection with the biological activities, such as breathing or the like of the subject K, for every electrode pad in the Cartesian coordinate system XYZ. Specifically, the displacement detector 84 is achieved using a magnetic sensor or the like, wherein it detects magnetism (one example of physical quantity) generated by the magnetic substance, which are previously provided to each of the electrode pads 4a to 4d, for every electrode pad, and magnetically detects each displacement of the electrode pads 4a to 4d based on the detected magnetism. The displacement detector 84 sends out each displacement detection result of the electrode pads 4a to 4d to the control unit 75 as displacement information. It is to be noted that the displacement information detected by the displacement detector 84 includes each amount of displacement and each displacement direction of the electrode pads 4a to 4d displaced in connection with the biological activities of the subject K, similar to the case of the fifth embodiment. The displacement detector 84 may be integrally arranged with the bed 64 for supporting the subject K as described above.

As described above, in the sixth embodiment of the present invention, the magnetic substance is further arranged to the electrode pad for human body communications, the displacement detector magnetically detects the displacement information of the electrode pad on the body surface displaced in connection with the biological activities of the subject based on the magnetism, which is the physical quantity generated outside the electrode pad by the magnetic substance, and other configurations are made in a manner similar to the aforementioned fifth embodiment. For this reason, operation effects similar to those of the fifth embodiment can be obtained, and the displacement information of the electrode pad can also be detected in a state of non-contact to the body surface of the subject or the electrode pad, thus allowing burden of the subject upon detecting the displacement of the electrode pad in connection with the biological activities of the subject to be reduced.

Figure 15:
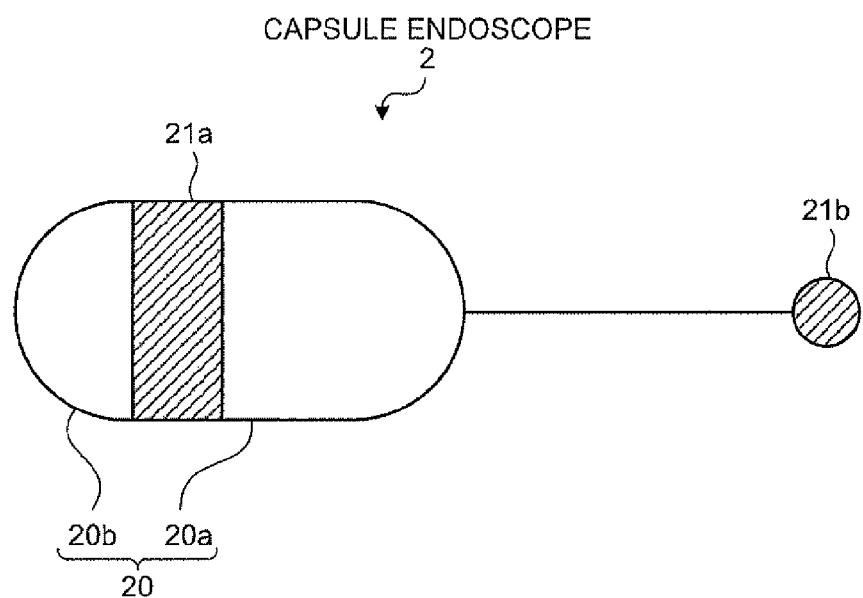
FIG. 15 is a schematic view showing a modified example of a capsule endoscope having a human body communication function.

It is to be noted that the capsule endoscope 2 having the human body communicating function is provided with the transmitting electrodes 21a and 21b for human body communications in the dome shape portions at both ends of the capsule-shaped casing 20 in the first to the sixth embodiments of the present invention, but not limited thereto. One of the pair of transmitting electrodes may be arranged on the outer surface of the capsule-shaped casing 20, and the other remaining transmitting electrode may be arranged at the tip of the cable extended from the capsule-shaped casing 20. In this case, the capsule endoscope 2 may be provided with the transmitting electrode 21a on the outer surface of the cylindrical casing 20a in the capsule-shaped casings 20 and near the dome-shaped casing 20b, and may be provided with the transmitting electrode 21b at the tip of the cable extended from the dome shape portion of this cylindrical casing 20a, as shown in FIG. 15, for example. This will allow a distance between the transmitting electrodes 21a and 21b to be further increased, and consequently, the electric field or the displacement current output by the transmitting electrodes 21a and 21b can be broadly formed inside the human body.

The transmitting electrodes 21a on the outer surface of the cylindrical casing 20a may be an opaque electrode achieved by a metal harmless to the human body similar to the transmitting electrode 21b. In addition, the aforementioned transmitting electrode 21a, which is a transparent electrode, may be arranged on the outer surface of the dome-shaped casing 20b, and the other remaining transmitting electrode 21b may be arranged at the tip of the cable extended from the dome shape portion of the cylindrical casing 20a. This allows the distance between the transmitting electrodes 21a and 21b to be increased as far as possible.

Figure 16:
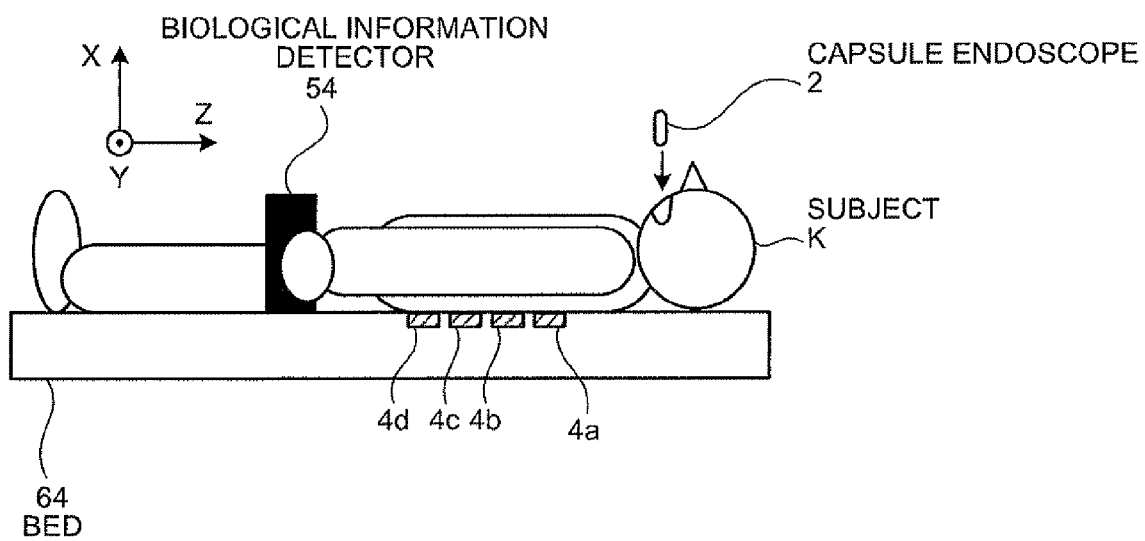
FIG. 16 is a schematic view illustrating a state where a biological information detector is projected from a subject supporting surface of a bed so as to allow a subject to grasp the detector.

Meanwhile, although the biological information detector 54 is exposed to the subject supporting surface of the bed 64 in the fourth embodiment of the present invention, the biological information detector 54 may be further protruded from the subject supporting surface of the bed 64 to a predetermined height. In this case, the biological information detector 54 is fixedly arranged onto the bed 64 in a form of protruding from the subject supporting surface of the bed 64 to a graspable height as shown in FIG. 16, for example. By causing the subject K to grasp the biological information detector 54, the body surface of the subject K and the biological information detector 54 can be easily contacted.

Figure 17:
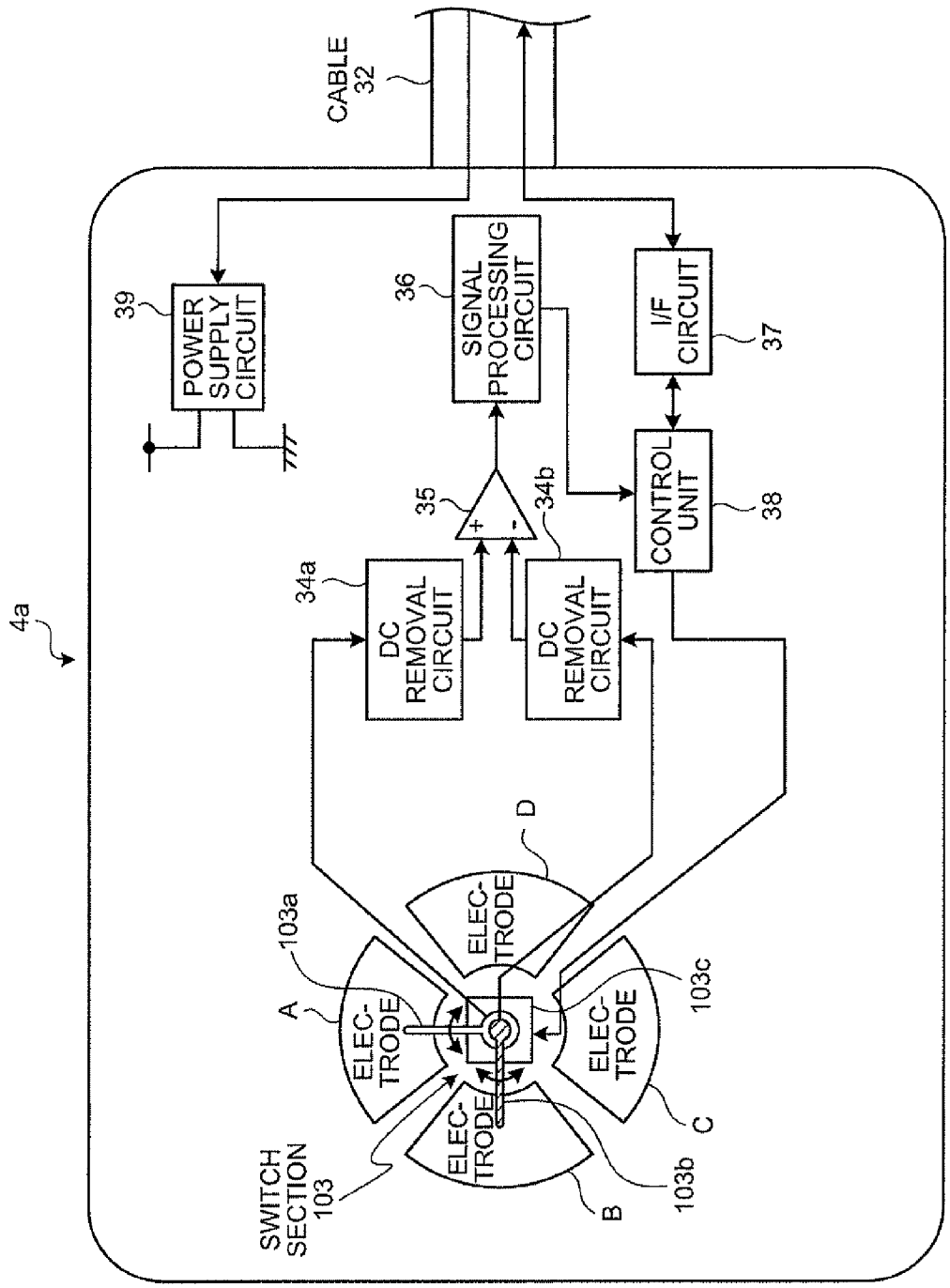
FIG. 17 is a schematic view showing one configuration example of an electrode pad provided with a rotary switch section.

Further, a pair of electrodes is electrically switched by the switching circuit (the switching circuits 33a and 33b or the switching circuits 47a and 47b) using a switching element or the like in the first to the sixth embodiments of the present invention, but not limited thereto. A pair of electrodes may be mechanically switched among the electrode groups of the electrode pad by respectively turning a pair of bar terminals connected to a pair of electrodes among the electrode groups. In this case, the electrode pad 4a has a switch section 103 provided with a pairs of bar terminals 103a and 103b connected to a pair of electrodes among four electrodes A to D, and a driving unit 103c as shown in FIG. 17, for example. The switch section 103 respectively turns the bar terminals 103a and 103b by the driving unit 103c to thereby sequentially select a pair of electrodes among four electrodes A to D. The driving unit 103c is controlled by the control unit 38, and turns the bar terminals 103a and 103b so as not to simultaneously connect the same electrode to the bar terminals 103a and 103b. Using the rotary switch section 103 makes it possible to easily form the receiving electrode for human body communications arranged to one electrode pad into multi-electrode. The above description may be similarly applied also to the electrode pads 4b to 4d or the electrode pad 42.

Additionally, the electrode pads 4a to 4d for human body communications and the biological information detector 54 are formed into different units in the third and fourth embodiments of the present invention, but not limited thereto. The electrode pads 4a to 4d and the biological information detector 54 may be integrated into single unit. In this case, the biological information detector 54 may be fixedly arranged near the electrode group of the electrode pad 4a to thereby arrange the electrode pad 4a onto the body surface of the subject K, and also to contact the biological information detector 54 and the body surface of the subject K to each other, for example.

Further, the amount of displacement of the electrode pads 4a to 4d on the body surface is directly measured by the displacement detector 74 in the fifth embodiment of the present invention, but not limited thereto. The displacement detector 74 may be a physical quantity measuring apparatus for measuring physical quantity generated when the electrode pads 4a to 4d (specifically, receiving electrode group for human body communications) are displaced in connection with the biological activities of the subject, such as stress, distortion amount, pressure, or the like to detect the displacement of the electrode pads 4a to 4d for every electrode pad based on the measured physical quantity.

Additionally, the displacement detector 84 measures the magnetism due to the magnetic substance previously fixedly arranged to each of the electrode pads 4a to 4d, and detects the displacement of the electrode pads 4a to 4d for every electrode based on this measured magnetism in the sixth embodiment of the present invention, but not limited thereto. The displacement detector 84 may be achieved using a temperature sensor or the like, and measure temperature which is the physical quantity produced outside by a heating element that is previously fixedly arranged to each of the electrode pads 4a to 4d to thereby detect the displacement of the electrode pads 4a to 4d for every electrode based on this measured temperature.

Alternatively, the displacement detector 84 may be achieved using a wireless receiver, an infrared ray receiver, or the like, and detect an electromagnetic wave or an infrared ray, which is the physical quantity produced outside by a transmitter that is previously fixedly arranged to each of the electrode pads 4a to 4d to thereby detect the displacement of the electrode pads 4a to 4d for every electrode based on the detected electromagnetic wave or infrared ray.

Further, the displacement detector 84 measures the magnetism due to the magnetic substance previously fixedly arranged to each of the electrode pads 4a to 4d, and detects the displacement of the electrode pads 4a to 4d for every electrode based on the measured magnetism in the sixth embodiment of the present invention, but not limited thereto. The displacement detector 84 may be an observation apparatus for observing optically or with an ultrasonic wave the displacement of the electrode pads 4a to 4d for every electrode pad. In this case, the displacement detector 84 is achieved using an observation apparatus, such as X ray apparatus, CT, imaging device, or ultrasonic device, and it captures the images of the electrode pads 4a to 4d on the body surface together with the subject K and detects the displacement of the electrode pads 4a to 4d based on the captured images. In this case, the displacement detector 84 can observe the shape (body type) of the subject K as well as the displacement of the electrode pads 4a to 4d.

Meanwhile, when the subject information (receiving voltage through the human body communications) is detected by each electrode group of the electrode pads 4a to 4d, the biological activity information of the subject K is always detected in the third and fourth embodiments of the present invention, but not limited thereto. The timing controller 55b may detect the biological activity information of the subject K for a predetermined period, and subsequently estimate a period while the variation of the biological activity information become small based on the detected biological activity information to thereby acquire the digital data of the detected voltage by the electrode pads 4a to 4d during the estimated period while the variation of the biological activity information is small. In this case, the timing controller 55b causes the position detector 7 to detect the position and direction of the capsule endoscope 2 at a timing when the variation of the biological activity information is estimated to be small.

Further, the bed 64 is exemplified as one example of the supporting member for supporting the subject K in the fourth embodiment of the present invention, but not limited thereto. The supporting member for supporting the subject K may be a chair or a supporting table which provides the subject K with a seating position, or may be an upright supporting table for supporting the subject K in a standing state.

In addition, the capsule endoscope 2 provided with the imaging function of capturing the in-vivo images of the subject, and the human body communicating function of transmitting the in-vivo images to the outside using the human body as the communication medium is exemplified as one example of the capsule medical device in the first to the sixth embodiments of the present invention, but not limited thereto. The capsule medical device of the capsule medical system in accordance with the present invention may be a capsule-type pH measuring device for measuring pH in the living body, as far as it has the information acquiring function of acquiring the subject information, and the human body communicating function of transmitting the subject information, may be a capsule-type medicine administration device provided with a function of spraying or injecting medicines in the living body, or may be a capsule-type extraction device for extracting substances in the living body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical system, comprising:
    a capsule medical device comprising a biological information acquiring unit for acquiring biological information of a subject, and a transmitting unit for outputting the biological information from a transmitting electrode through a living body;
    at least one electrode pad arranged on a body surface of the subject and comprising a plurality of receiving electrodes for detecting the biological information;
    a receiving electrode switching unit that switches a pair of receiving electrodes among the plurality of receiving electrodes;
    a control unit that controls operations of the receiving electrode switching unit; and
    a position detector that detects a position of the capsule medical device within the subject based on the biological information detected by the electrode pad and position coordinate data of the plurality of receiving electrodes.

2. The capsule medical system according to claim 1, wherein the plurality of receiving electrodes includes three or more receiving electrodes, and
    the position detector detects at least one of the position and direction of the capsule medical device within the subject based on detection values of different directions detected by the three or more receiving electrodes.

3. The capsule medical system according to claim 1, wherein the receiving electrode switching unit is arranged within the electrode pad.

4. The capsule medical system according to claim 1, further comprising an A/D conversion processing unit that is arranged within the electrode pad and converts into digital data the biological information detected by the pair of receiving electrodes,
wherein the position detector detects the position of the capsule medical device within the subject based on the digital data and the position coordinate data of the plurality of receiving electrodes, and
the control unit is arranged within the electrode pad.

5. The capsule medical system according to claim 1, wherein the transmitting electrode is a transparent electrode.

6. The capsule medical system according to claim 1, wherein the transmitting electrode includes a first transmitting electrode provided at an outer surface of a capsule-shaped casing of the capsule medical device, and a second transmitting electrode provided at a tip of a cable extended from the capsule-shaped casing.

7. The capsule medical system according to claim 1, wherein the electrode pad is provided with a flexible circuit board for fixedly arranging the plurality of receiving electrodes at a known position coordinate within the body surface of the subject.

8. The capsule medical system according to claim 1, further comprising
a biological information detector that detects biological activity information of the subject, and
a timing controller that calculates variation of the biological activity information based on the biological activity information sequentially detected by the biological information detector, and causes the position detector to detect the position of the capsule medical device at a timing when the calculated variation of the biological activity information is a predetermined threshold value or less.

9. The capsule medical system according to claim 8, wherein the biological information detector is integrally arranged with a supporting member for supporting the subject.

10. The capsule medical system according to claim 8, wherein the biological information detector is integrally arranged with the electrode pad.

11. The capsule medical system according to claim 1, further comprising
a displacement detector that detects an amount of displacement of the plurality of receiving electrodes displaced by biological activities of the subject; and
a correction processing unit that corrects the position coordinate data of the plurality of receiving electrodes based on the amount of displacement detected by the displacement detector,
wherein the position detector detects the position of the capsule medical device based on the position coordinate data of the plurality of receiving electrodes corrected by the correction processing unit, and the biological information detected by the electrode pad.

12. The capsule medical system according to claim 1, wherein the electrode pad is circular.

13. The capsule medical system according to claim 1, wherein the plurality of receiving electrodes are arranged on a same circumference.

14. The capsule medical system according to claim 1, wherein the receiving electrodes are arranged in a circumferential direction on a part of the body surface of the subject, and position coordinate data of the part is obtained in advance.

* * * * *